United States Patent [19]
Verdonk

[11] Patent Number: 5,640,961
[45] Date of Patent: Jun. 24, 1997

[54] DEVICE WITH ASPHERICAL COMPENSATION FOR FOCUSING ULTRASOUND

[75] Inventor: Edward Verdonk, San Jose, Calif.

[73] Assignee: Hewlett-Packard Company, Palo Alto, Calif.

[21] Appl. No.: 533,430

[22] Filed: Sep. 25, 1995

[51] Int. Cl.$^6$ ............................................. A61B 8/00
[52] U.S. Cl. ............................................. 128/662.06
[58] Field of Search .................. 128/662.03, 662.06, 128/662.05, 663.01; 73/623

[56] References Cited

U.S. PATENT DOCUMENTS

| | | | |
|---|---|---|---|
| 4,572,201 | 2/1986 | Kondo et al. | 128/660 |
| 4,794,931 | 1/1989 | Yock | 128/305 |
| 4,917,097 | 4/1990 | Proudian et al. | 128/662 |
| 5,000,185 | 3/1991 | Yock | 128/662 |
| 5,176,141 | 1/1993 | Bom et al. | 128/662 |
| 5,186,177 | 2/1993 | O'Donnell et al. | 128/662 |
| 5,240,003 | 8/1993 | Lancee et al. | 128/662 |
| 5,271,402 | 12/1993 | Yeung et al. | 128/662 |
| 5,284,148 | 2/1994 | Dias et al. | 128/662 |
| 5,291,090 | 3/1994 | Dias | 310/334 |
| 5,421,338 | 6/1995 | Crowley et al. | 128/662.06 |

OTHER PUBLICATIONS

Kino, G.S., "Wave Propagation with Finite Exciting Sources", *Acoustic Waves*, Prentice Hall, 1987, Chapter 3, pp. 155–163.
LaLonde, R. et al., "Field Conjugate Acoustic Lenses for Ultrasound Hyperthermia", *IEEE Trans. on Ultrasonics*, vol. 40, No. 5, Sep. 1993, pp. 592–602.
Lockwood, G. et al., "Fabrication of High Frequency Spherically Shaped Ceramic Transducers", *IEEE Trans. on Ultrasonics*, vol. 41, No. 2, Mar. 1994, pp. 231–235.
MacAlpin, R. et al., "Human Coronary Artery Size During Life", *Dept. of Medicine and Radiology, School of Medicine, University of California, Los Angeles*, Apr. 1973, pp. 567–576.

*Primary Examiner*—George Manuel

[57] ABSTRACT

An ultrasound probe having a substantially cylindrical acoustic case for intraluminal application in an object, a method of making such a probe, and a method of focusing ultrasound are provided. The probe has a substantially cylindrical acoustic case with a central axis and an ultrasonic transducer unit positioned in the acoustic case. The ultrasonic transducer unit is rotatable about the central axis of the acoustic case to transmit or receive ultrasonic beams in a direction at an angle to the central axis. The transducer unit has a transducer for generating or receiving ultrasound, a shaft operatively connected with the transducer and having an axis substantially coincident with the central axis for rotating the transducer around the central axis, and an aspherical lens coupled with the transducer in the acoustic case to reduce the distortion by the focusing effect of the acoustic case on ultrasound. In a preferred embodiment, the aspherical shape of the aspherical lens is determined by a method including: selecting a focal point at the target area as a hypothetical source of a hypothetical beam of ultrasound, calculating the velocity potential on the transducer based on the hypothetical beam of ultrasound, and calculating the aspherical shape of the aspherical lens based on the velocity potential.

24 Claims, 20 Drawing Sheets

DEVICE WITH ASPHERICAL COMPENSATION FOR FOCUSING ULTRASOUND

FIELD OF THE INVENTION

The present invention relates to ultrasound probes that provide an intravascular ultrasound (IVUS) image. More particularly, the present invention relates to ultrasound probes, methods of making and using such probes with a minimal amount of image aberration in application.

BACKGROUND

To combat heart disease, a leading cause of death and disability in many countries, physicians require detailed data on the vasculature of the heart. In vivo, intravascular ultrasonic imaging (IVUS) offers a relatively benign method of obtaining such information. Ultrasonic imaging involves transmitting an ultrasonic acoustic wavefront pulse into a body and detecting the reflection of that pulse. Reflections occur at boundaries where acoustic impedance changes. The times at which reflections are received by a transducer correspond to the depths of these impedance boundaries. By stepping a transducer through a selected angle, one can obtain a two-dimensional (angle and depth) ultrasound image that is essentially a map of impedance boundaries. The intensity and position of these impedance boundaries can then be interpreted to characterize the condition of a vessel and its immediate environment.

The quality of the image is strongly affected by its resolution, which is in turn determined by the ultrasound wavelengths used to examine a body. Shorter wavelengths, which correspond to higher frequencies, provide higher resolution images. However, higher frequencies attenuate more rapidly, limiting their use for depth examinations. Accordingly, high frequency transducers are most appropriate for high-resolution relatively shallow imaging. For example, whereas 5–20 MHz ultrasound frequencies are useful for prenatal and peripheral vessel examinations, 30 MHz and higher are desired for intravascular examinations of cardiac vasculature.

In recent years, cardiologists have increasingly come to appreciate the diagnostic value of obtaining cross sectional images of coronary arteries by the method of IVUS. Currently there are two general types of IVUS catheter systems. First, there is the synthetic aperture approach. For example, U.S. Pat. No. 4,917,097 (Proudian et al.) and U.S. Pat. No. 5,186,177 (O'Donnell) teach how the ultrasonic beam is steered electronically from a transducer using the approach of synthetic aperture. A second type is the mechanically rotated type where the image is scanned by mechanical motion. The mechanically rotated types have three subclasses. In a first subclass, either the distal (remote from the operator) transducer or a mirror is rotated from the proximal end of the catheter by an extended drive shaft, and a proximal motor (as taught by Yock in U.S. Pat. No. 4,794,931 and U.S. Pat. No. 5,000,185). In a second subclass, the rotation is confined to the distal end, where either a miniature motor is used to rotate the transducer (U.S. Pat. No. 5,240,003 and U.S. Pat. No. 5,176,141 (Bom)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide which conducts the sound to the distal end (e.g., U.S. Pat. No. 5,284,148 (Dias and Melton)).

The most prevalent type of IVUS catheter in use today is the mechanically rotated system with a planar single element transducer placed at the distal end of the catheter. A reason for this preference is the superior image quality compared with current synthetic aperture systems.

Regarding the pressure field of a planar transducer radiating into a homogenous liquid, the transition distance, N from the near-field (i.e., Fresnel region) to the far-field (i.e., Fraunhofer region) is commonly represented by $$N = d^2/4\lambda \qquad (1)$$

where d is the diameter of a circular transducer (or the width of a square transducer) and $\lambda$ is the wavelength of sound. FIG. 1 illustrates the transition region or focal zone (about the transition distance). In FIG. 1, an ultrasound probe 10 having a transducer 16 mounted on a rotatable shaft 14 encircled by a substantially cylindrical case (or sheath) 20 is shown. The probe is positioned inside the lumen 22 of a blood vessel 26 in the body (not shown) of a patient. The transducer 16 contains a single transducer element (although a multielement transducer can also be used). The ultrasonic field produced by the transducer has a Fresnel region A, a natural focal point (located at 30) and a Fraunhofer region B as shown in FIG. 1. The shaft can be rotated in a direction D to sweep the ultrasound in a direction of rotation C. FIGS. 2A and 2B show the transducer in portion.

As indicated by Equation (1), both the physical size and operating frequency of the transducer affect the axial location of the focal zone. Imaging of coronary arteries demands high frequency transducers, usually in the 20 to 30 MHz range, to achieve adequate axial (temporal) resolution whereby a clinician can resolve layers of the arterial wall. Physical size of IVUS catheters are continually being reduced so that they may be passed further down the coronary arterial tree or through narrower obstructions. Lower limits on catheter size are set by the ability to fabricate very small transducers and also by the fact that the transducer's electrical impedance rises and sensitivity drops with decreases in area. Currently the smallest available IVUS catheters are approximately 3.0 French in size (~1 mm diameter). Table 1 tabulates transition distances for various size (i.e. diameter) transducers and frequencies that can be used to image coronary arteries. The data assume the transducers to be radiating into water (v=1.5 mm/µsec) which has an acoustic impedance and velocity similar to mammalian tissue.

TABLE 1

| Diameter of Transducer | 0.4 mm | 0.6 mm | 0.8 mm | 1.0 mm | 1.2 mm |
|---|---|---|---|---|---|
| 10 MHz | 0.27 | 0.60 | 1.07 | 1.67 | 2.40 |
| 15 MHz | 0.40 | 0.90 | 1.60 | 2.50 | 3.60 |
| 20 MHz | 0.53 | 1.20 | 2.13 | 3.33 | 4.80 |
| 25 MHz | 0.67 | 1.50 | 2.67 | 4.17 | 6.00 |
| 30 MHz | 0.80 | 1.80 | 3.20 | 5.00 | 7.20 |

Normal coronary arteries have diameters (mean±standard deviation) of 4.0±0.7 mm in the left main region. They narrow to 3.4±0.5 mm in the left anterior descending portion and to 3.0±0.7 mm in the circumflex portion of the coronary arterial tree (MacAlpin, et al., *Radiology*, vol. 108, Sept. 1973, pp. 567–576). Diseased coronary arteries have narrower lumens, possibly too tight for existing IVUS catheters to pass. Assuming that the catheter is positioned in the center of the arterial lumen, then it is desired that N falls somewhere between the outer wall of the catheter (~0.5 mm radius, currently the smallest IVUS catheter) and the vessel wall (~2.0 mm radius, the largest anticipated radius of a normal coronary artery). For a chosen operating frequency, the selection of the diameter of the transducer when using a planar transducer is clearly limited.

Kondo et al., in U.S. Pat. No. 4,572,201, teach the use of an elliptically shaped transducer to "improve the resolution in the direction parallel to the axis of rotation" but do not address the effect of the "acoustic case" on the focal zone characteristics. In U.S. Pat. No. 5,291,090, Dias recognizes the distortion that the sheath has on the focus and suggests the use of an elliptically shaped transducer to correct for it. However, he does not teach how the dimensions of the transducer should be determined. Lockwood et. al. (*IEEE UFFC*, 1994, 41(2), pp 231-235) have produced spherically-shaped, high frequency transducers but operate them without a sheath. Their transducers are also too large for intravascular imaging in vivo. What is needed is a technique to control the focal zone of intravascular ultrasound probes having sheaths, thereby to obtain an optimal cross sectional image of the vessel under examination.

SUMMARY

Ultrasound probes for intraluminal application (e.g., in a patient) often have sheaths. A sheath is a substantially cylindrical case typically used for protecting the blood vessel (i.e., arterial wall) from being damaged by the probe. The present invention meets a need in the prior art and provides a technique of controlling the focal zone of an ultrasound probe by taking into consideration the effect of intervening structures, such as the catheter sheath, on the pressure fields generated. More specifically, this invention provides an ultrasound probe (with a sheath) that results in a uniform pressure field in the focal zone and a method of making the probe. The method of making such an ultrasound probe includes mounting a transducer on a rotatable shaft; providing an aspherical means (such as an aspherical lens); and positioning the rotatable shaft, the transducer, and the aspherical means in spatial relation to the sheath (e.g., securing the aspherical lens to the rotatable shaft and the transducer inside the sheath) such that the asymmetric focusing effect by the sheath is reduced by the aspherical lens. The transducer can generate or receive ultrasound. In a preferred embodiment, the transducer generates and receives ultrasound. The shaft has an axis and the substantially cylindrical case has an axis substantially coincidental to the axis of the shaft for rotatable transmission or reception of ultrasound. Electronic means (e.g., wires, oscillators, amplifiers, and the like) can also be present for coupling with the transducer to transmit or receive ultrasound.

The present invention further provides a method for focusing a beam of ultrasound at a target area of an object using an ultrasound probe with a substantially cylindrical case around the transducer of the probe. The case has a central axis and the transducer is rotatable about the central axis of the case. The method includes transmitting the beam of ultrasound through the case and focusing the beam of ultrasound through an aspherical means to reduce the distorting effect by the case.

The aspherical shape of the aspherical means (e.g., lens) can be determined by selecting a focal point at a target area, using the focal point as a hypothetical source of ultrasound, and calculating the required velocity potential on the transducer surface. By taking into consideration the focusing effect of the sheath, its distorting effect can be compensated.

The intraluminal ultrasound probes and methods of the present invention can be advantageously used to tailor the focal zone characteristics of IVUS catheters in a controlled fashion. As previously stated, high frequencies are useful but do not penetrate deep into the body. To obtain high resolution and sharp images using ultrasonic probes, it is important to direct an ultrasonic beam to a target tissue in an appropriate focal zone. Moreover, it is beneficial that the ultrasonic beam in this focal zone have uniform pressure field since nonuniformity in pressure will adversely affect the quality of the ultrasound reflected by the tissue and received by the receiving transducer.

As indicated in FIG. 1, a single element transducer of diameter d introduces ultrasonic waves of wavelength $\lambda$ into a fluid. In the absence of a sheath, the expression $N=d^2/4\lambda$ governs where the so-called "natural focus," N, of the transducer lies. N defines at what axial range the ultrasonic field transitions from the near field, (associated with complicated pressure field) to the far field (associated with a diverging of the beam and monotonic drop in the intensity of sound) occurs. The pressure distribution in the ultrasonic near-field is very complex (i.e., very nonuniform), containing numerous peaks and nulls. Moreover, the peaks may be off-axis (i.e., off the central region of the beam), resulting in the imaging of structures peripheral to the actual region of interest. It is therefore desirable to image at or beyond the transition distance.

In general, the highest quality images are obtained by placing the focal zone of the transducer in the region of interest (e.g., the arterial wall) to take advantage of the minimum lateral dimension (improved resolution) and maximum sound intensity (improved signal to noise ratio). Hence, the ability to tailor the focal zone of a transducer (having a given diameter and frequency), particularly a transducer encircled by a sheath, is useful. This can be accomplished by the aspherical means (e.g., lens or curved transducer) according to the present invention. In fact, using a probe (either with an aspherical lens or curved transducer) in accordance with the present invention, the focal zone may be brought in closer than the distance N. In practice the focal zone would preferably be positioned somewhere between the outer radius of the substantially cylindrical case (or catheter sheath) and N.

The method of making the ultrasound probe in accordance of the present invention explicitly incorporates the effects of the catheter sheath on the acoustical beam. Heretofore the sheath has been assumed to cause negligible changes to the ultrasonic pressure fields relative to the fields produced without the presence of a sheath. It has been shown (e.g., the theoretical beam plots illustrated in FIGS. 5 and 6) that a sheath can in fact have a significant effect on the overall quality of the beam. For example, the rotational symmetry of the ultrasonic fields inherent to a circular (i.e., disk-shaped) transducer is lost by the addition of a catheter sheath. The method described herein can be used to restore that symmetry if desired.

The ultrasound probe of the present invention can be used to provide cross sectional images of coronary arteries which take advantage of the optimal available resolution, maximum signal to noise ratio, and symmetry of the ultrasonic beam. Specifically, the ultrasound probe places the focal zone of an intravascular imaging catheter at a specified distance from the face of the transducer. What distinguishes this probe from prior art devices is the presence of an aspherical means (e.g., lens) to compensate for the distorting focusing effect of the catheter sheath. The invention may be applied to any IVUS catheter that results in passage of sound through a catheter sheath, be it a multielemented synthetic aperture catheter, a mechanically rotating catheter with either a single transducer at the distal end of the catheter, or an acoustic waveguide wherein a transducer is located at the proximal end of the catheter and a virtual transducer is formed at the distal end.

BRIEF DESCRIPTION OF THE DRAWINGS

The following figures which show embodiments of the present invention are included to better illustrate the present invention. In these figures, wherein like numerals represent like features in the several views.

DETAILED DESCRIPTION OF THE INVENTION

The ultrasound probe of the present invention has an aspherical means (e.g., lens) to compensate for the distortion of an ultrasonic beam caused by the focusing effect of a sheath encircling the shaft and the transducer.

Preferred Embodiment of the Probe

Figure 3:
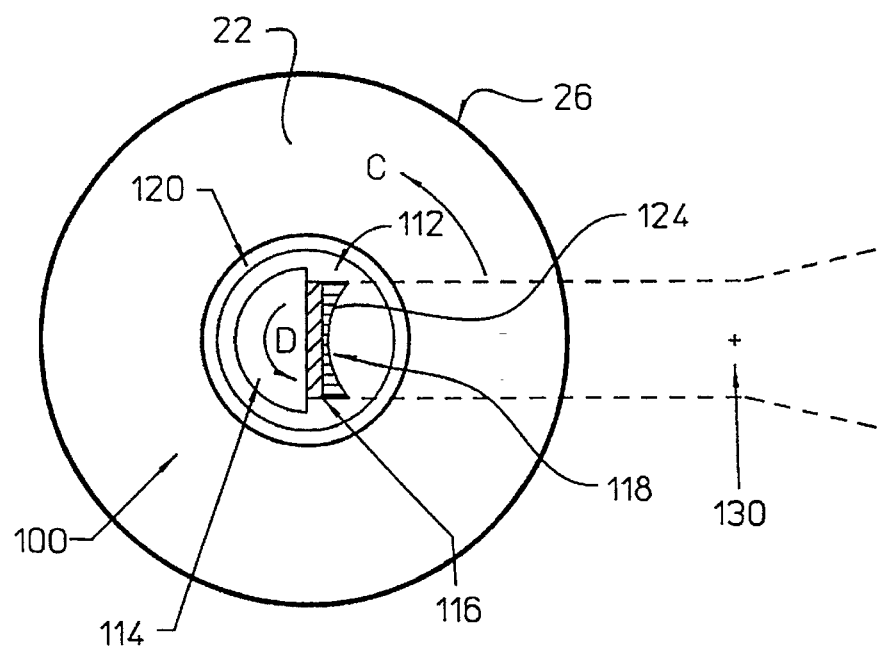
FIG. 3 shows a cross-sectional view of an embodiment of the ultrasound probe of the present invention positioned inside a blood vessel.

As shown in FIG. 3, which shows a preferred embodiment of the ultrasound probe of the present invention, the ultrasound probe 100 of the present invention has a shaft 114 rotatable by a rotating means (not shown) such as a electrical motor, pneumatic drive, and the like. A transducer 116 is mounted on the rotatable shaft 114 for transmitting and receiving ultrasound. The transducer 116 preferably has a single transducer element for ease of construction. However, a plurality of transducer elements located on a surface of the transducer can be used. Preferably, the transducer has a planar surface (i.e., the transducer is a planar transducer) that operates in a piston mode (i.e., all the particles of the whole transducer vibrate in phase).

An aspherical lens 118 is mounted on the transducer 116 on a surface remote from the rotating shaft 114. The aspherical lens 118 has an aspherical surface 124 facing outwardly from the axis of the shaft 114 and has a planar surface for abutting and attaching to the planar transducer 116. The shaft 114, transducer 116, and lens 118 are rotatable as a unit 112 inside a cylindrical case (or sheath) 120, which protects the blood vessel from the rotating action of the rotating unit (i.e., the shaft, transducer, and lens). The shaft 114 has an axis which is substantially coincident with the axis of the sheath 120 so that when the shaft rotates (and therefore the rotatable transducer unit 112), the rotatable transducer unit 112 rotates substantially along the axis of the sheath near the transducer. It is to be understood that the shaft 114 and the sheath 120 are preferably flexible so that their axes are related to their general shapes and are not necessarily straight along their entire lengths.

Figure 1:
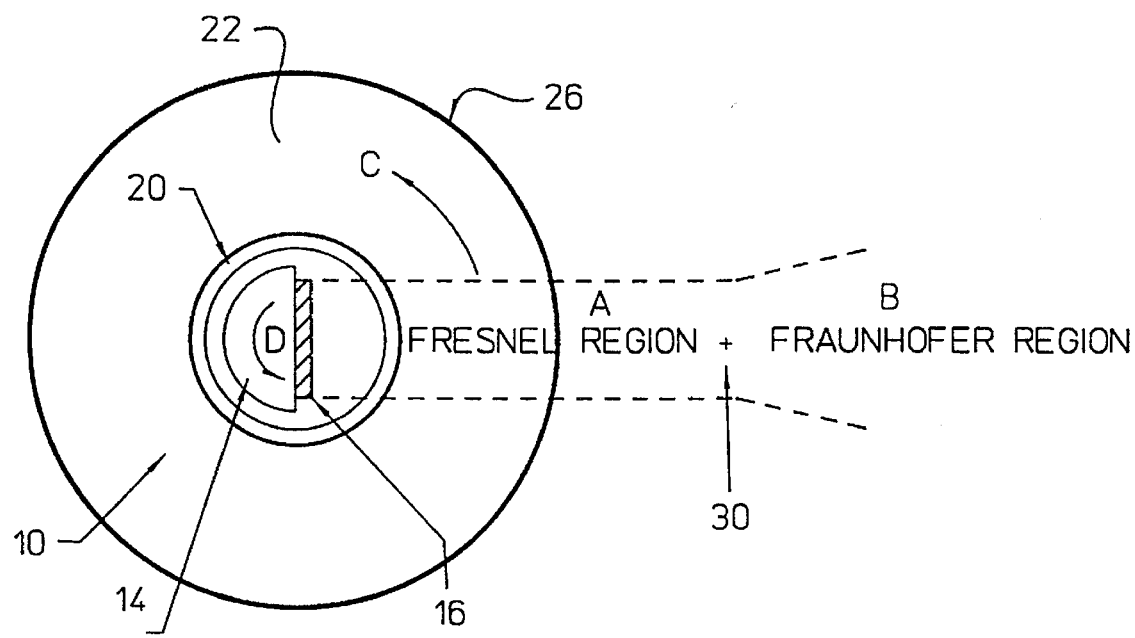
FIG. 1 shows a cross-sectional view of a prior art ultrasound probe positioned inside a blood vessel.

As the rotating unit rotates in a direction D, the transducer 116 transmits and receives ultrasound. Ultrasound transmitted in this way is swept in a direction C about the axis of the shaft 114. With reference to FIG. 2B, the ultrasound beam is transmitted at an angle β relative to the normal direction to the sheath. The angle β is exaggerated in FIG. 2B to show details of the probe. A small value of β (preferably approximately 10°) is made to reduce reverberations between the transducer and the sheath. Larger values of β may be chosen to facilitate a "look ahead" capability to assist in catheter guidance. It is to be understood that although 10° is more preferred, a preferred range of β is about 0° to 30°. Since the aspherical lens compensates for the focusing effect of the sheath 120, ultrasound that is transmitted from the transducer through the aspherical lens is focused at location 130 (see FIG. 3), which preferably is located at or proximate to location 30 of FIG. 1, assuming probe 10 and probe 100 have the same shaft and transducer.

Effect of an Aspherical Means in the Ultrasonic Probe

Single element catheters give good image quality, but diffraction calculations suggest that the use of a lens in conjunction with a planar transducer or the use of a curved (i.e., concave) transducer offers significant improvements in the resulting pressure field over the field produced by a planar transducer alone. By using a lens in combination with a planar transducer, one can employ a larger diameter transducer than otherwise and still achieve the target focus. FIGS. 4, 5, 6 and 7 compare the pressure fields produced with and without the use of a focusing lens. Each plot shows isopressure lines at the −3, −6, −10, and −20 dB levels (represented by broken lines labeled as p208, p206, p204, p202, respectively). However, it is contemplated that, instead of using an aspherical lens, other means can be used to compensate for the distortion caused by the sheath. For example, the transducer can be curved or the sheath can have a portion with nonuniform thickness to achieve the focusing effect in a way analogous to the aspherical lens to compensate for the distortion of the sheath. However, because of the relative complexity of constructing and positioning an aspherically curved transducer or a sheath with a portion of nonuniform thickness, an aspherical lens is preferred.

Figure 2A:
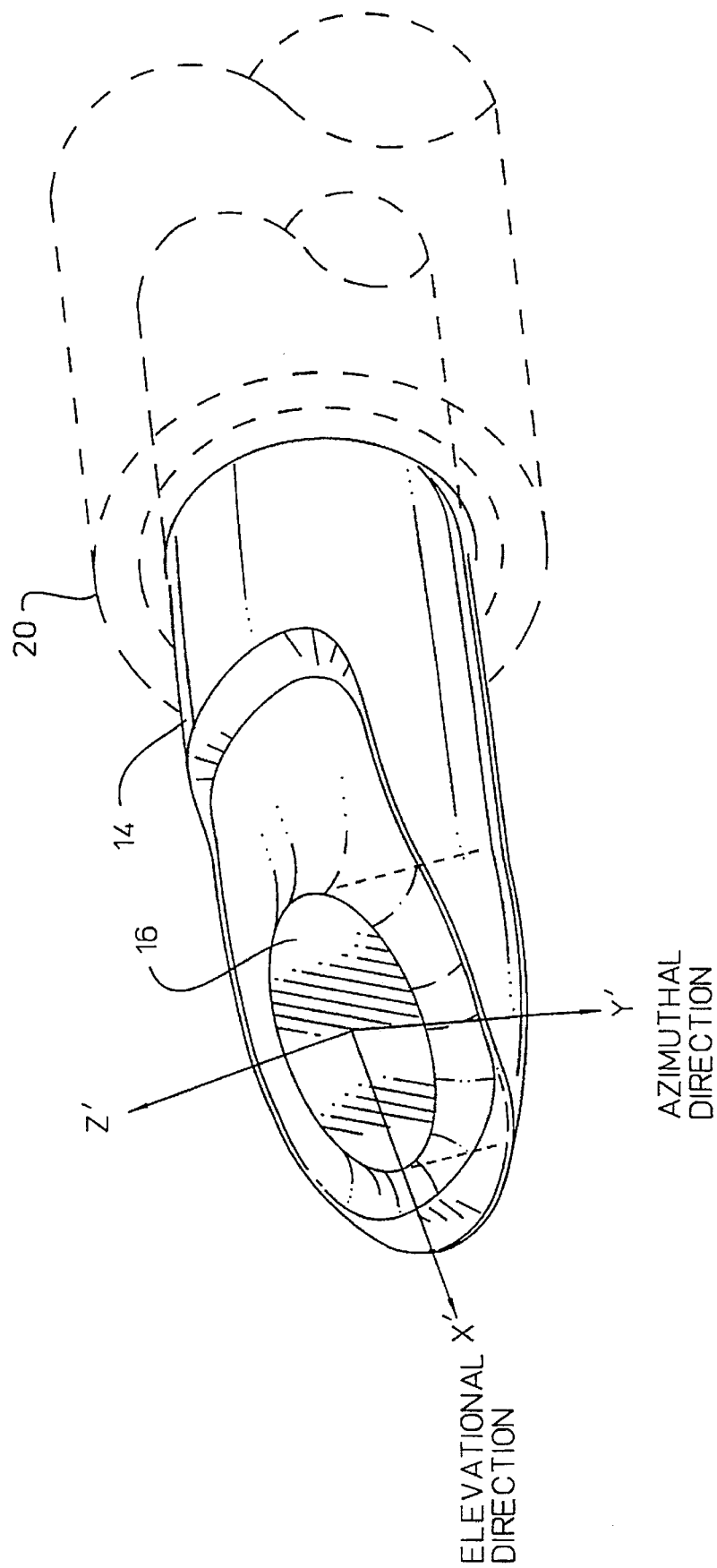
FIG. 2A shows an isometric view in portion of the prior art probe of FIG. 1, showing the x', y', and z' axes and the azimuthal and elevation directions.
Figure 2B:
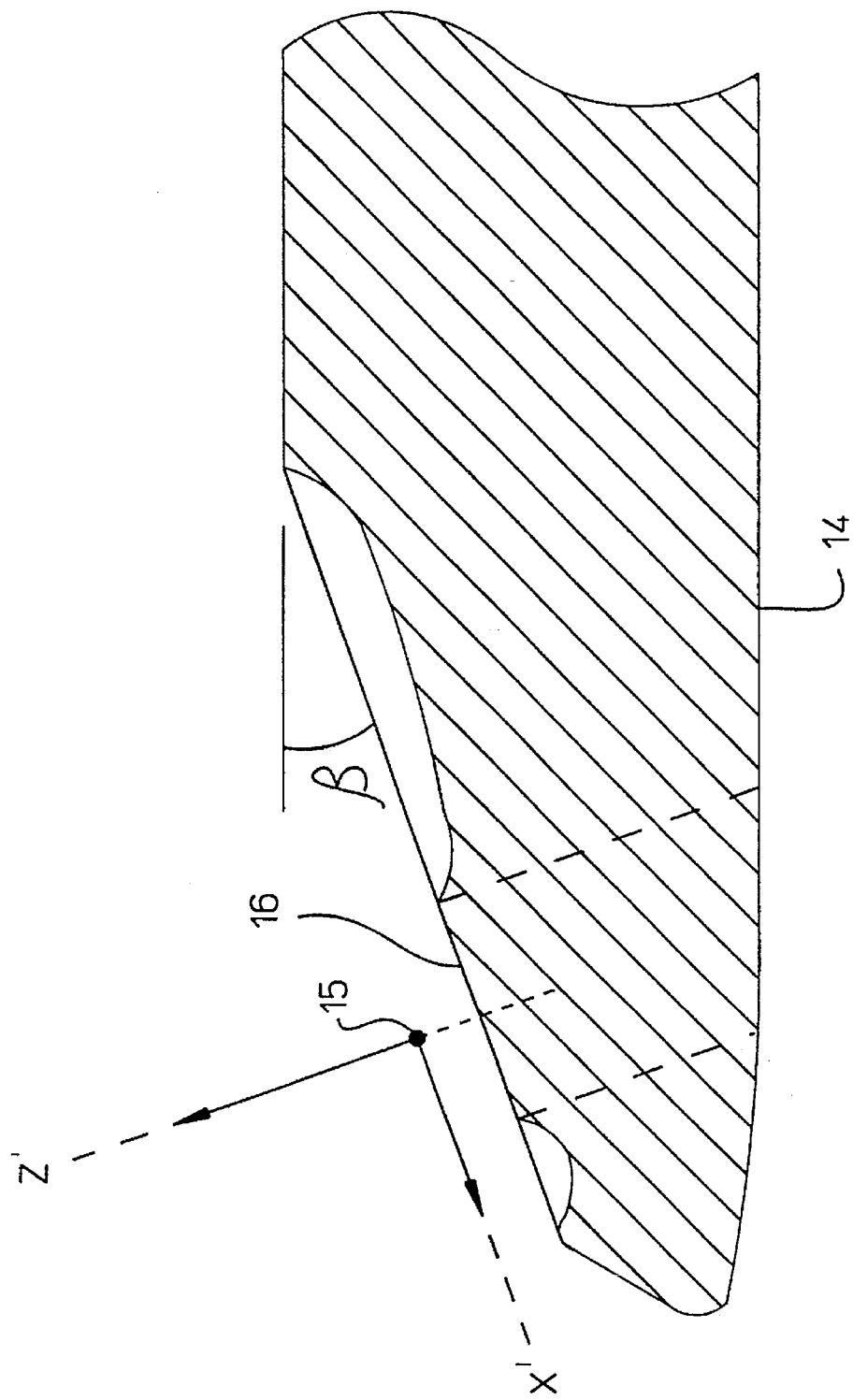
FIG. 2B shows a side view of the probe of FIG. 2A in portion (omitting the sheath for the sake of clarity)

FIGS. 2A and 2B illustrate the azimuthal and elevational directions for field plots including the catheter sheath. The coordinate axes x', y', and z' have their origin on the face of the transducer. The axis z' is coincident with the axis (normal) of the transducer. Because of the forward tilt of the transducer (i.e., β is not 0°), z' is not perpendicular to the rotational axis of the catheter. The elevational and azimuthal directions are defined to lie along the x' axis and the y' axis respectively. In FIG. 2B, the y' axis is shown by arrow 15 which is normal to the page.

Figure 4:
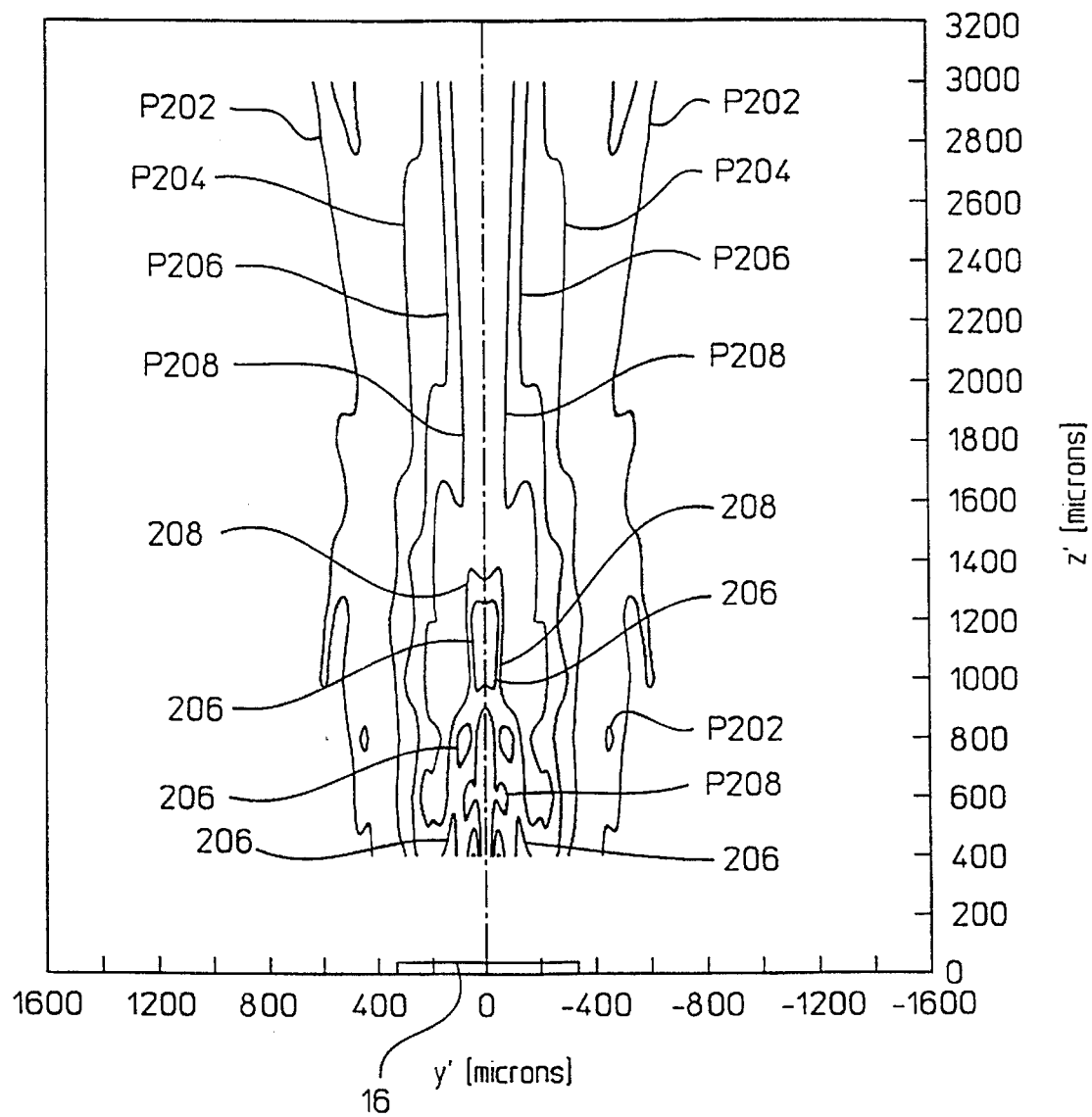
FIG. 4 shows a graphical representation of the calculated azimuthal pressure contours of a 3.5 French, 30 MHz intravascular catheter having no sheath and no means for compensating for the distorting effect of a sheath.

Diffraction calculations for single element transducers radiating into water have been extensively studied and are well understood. As an illustration of these calculations, FIG. 4 is a contour plot of the pressure field produced by a circular transducer of 0.67 mm diameter operating in continuous wave (CW) mode at 30 MHz and radiating into water. The data have been adjusted to mimic the effect of normal time gain compensation (TGC) as commonly available in consoles of intravascular imaging apparatuses. Generally, the TGC's are adjusted to make the maximum signal amplitude at each depth equal (adjusted to 1 for these plots). That is, pressures calculated at points along each line of fixed z' value were normalized by the maximum pressure determined in a plane of the same fixed z'. In this way, a flat response with increasing range (z' here) is achieved. The fields are symmetric for rotation about the axis of the transducer (which is in a direction somewhat normal to the axis of the rotatable shaft). The axial focal point is located at z'=2230 μm.

Less well understood is the effect that intervening structures between the transducer and field points of interest have on the properties of the ultrasonic beam. For example, the effect of the catheter sheath on the location and dimensions of the focal zone of IVUS catheters. The transducer with its associated wiring and/or drive cable shaft (or cable) of an intravascular catheter is contained within a concentric sheath. The sheath serves two purposes. First, it provides mechanical support to the drive cable to prevent it from knotting up and to allow it to be guided along a tortuous route to reach the imaging site. Second, the sheath protects the delicate intimal layer of the artery from abrasion by the spinning drive cable and transducer.

Most sheaths are formed from one or more layers of plastic material (for example, methylpentene copolymer (e.g., TPX), polytetrafluoroethylene (TEFLON), polyethylene, polyurethane) which have a higher speed of sound than water (or blood). For example, in FIGS. 5–6, the sheath 20 has an outer layer 20A and an inner layer 20B. Similarly, in FIG. 7, the sheath 120 has layers 120A and 120B. This velocity differential, coupled with the cylindrical shape will cause the sheath to act as a focusing lens in the azimuthal direction. In the orthogonal direction in FIG. 2, referred to here as the elevational direction, one expects little or no focusing of the ultrasonic beam. Thus a circularly shaped, flat transducer surrounded by a cylindrical sheath is expected to produce an asymmetric beam outside of the sheath.

Figure 5A:
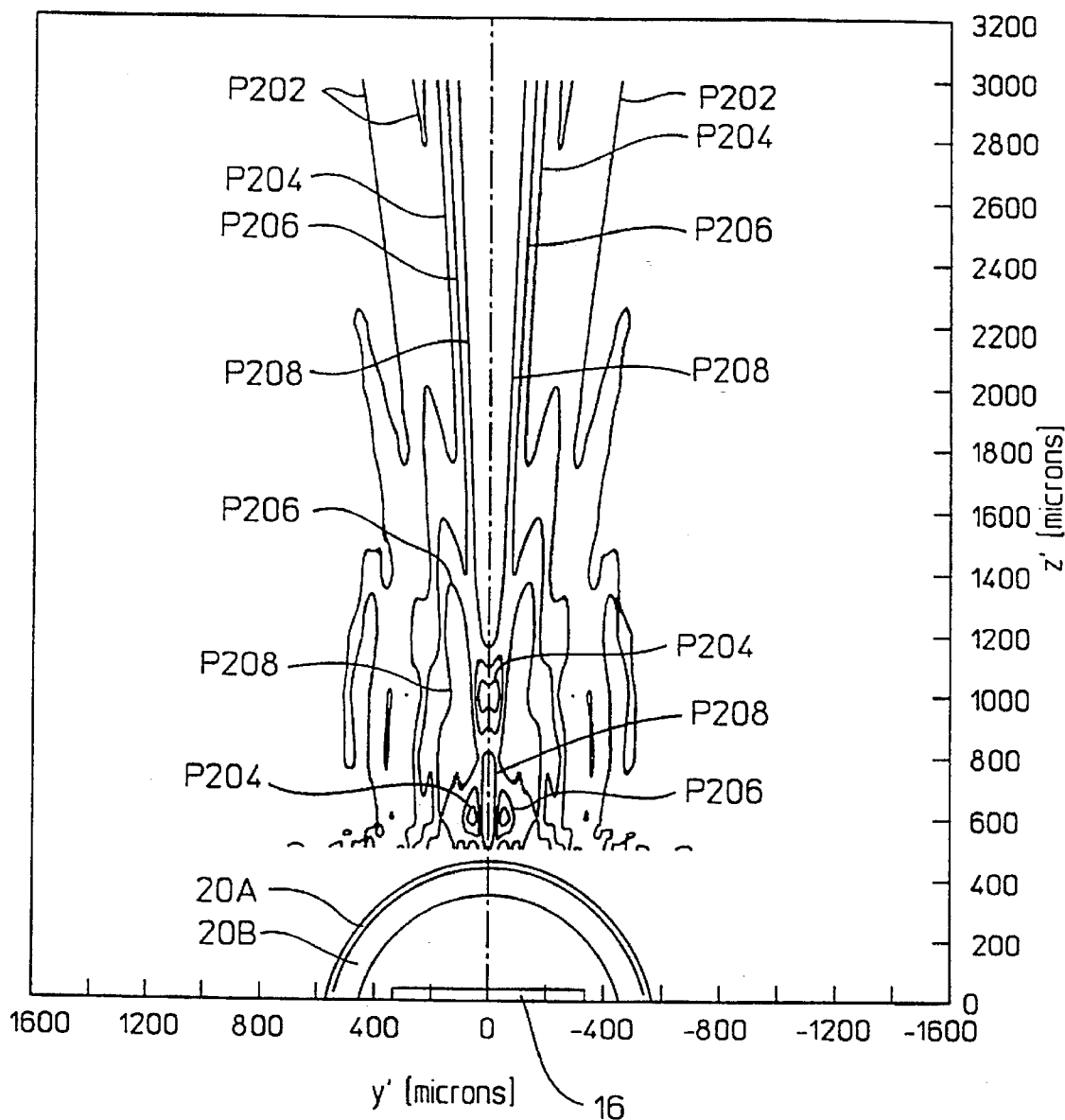
FIG. 5A shows a graphical representation of the calculated azimuthal pressure contours of a 3.5 French, 30 MHz intravascular catheter having a sheath and no means for compensating for the distorting effect of a sheath.
Figure 5B:
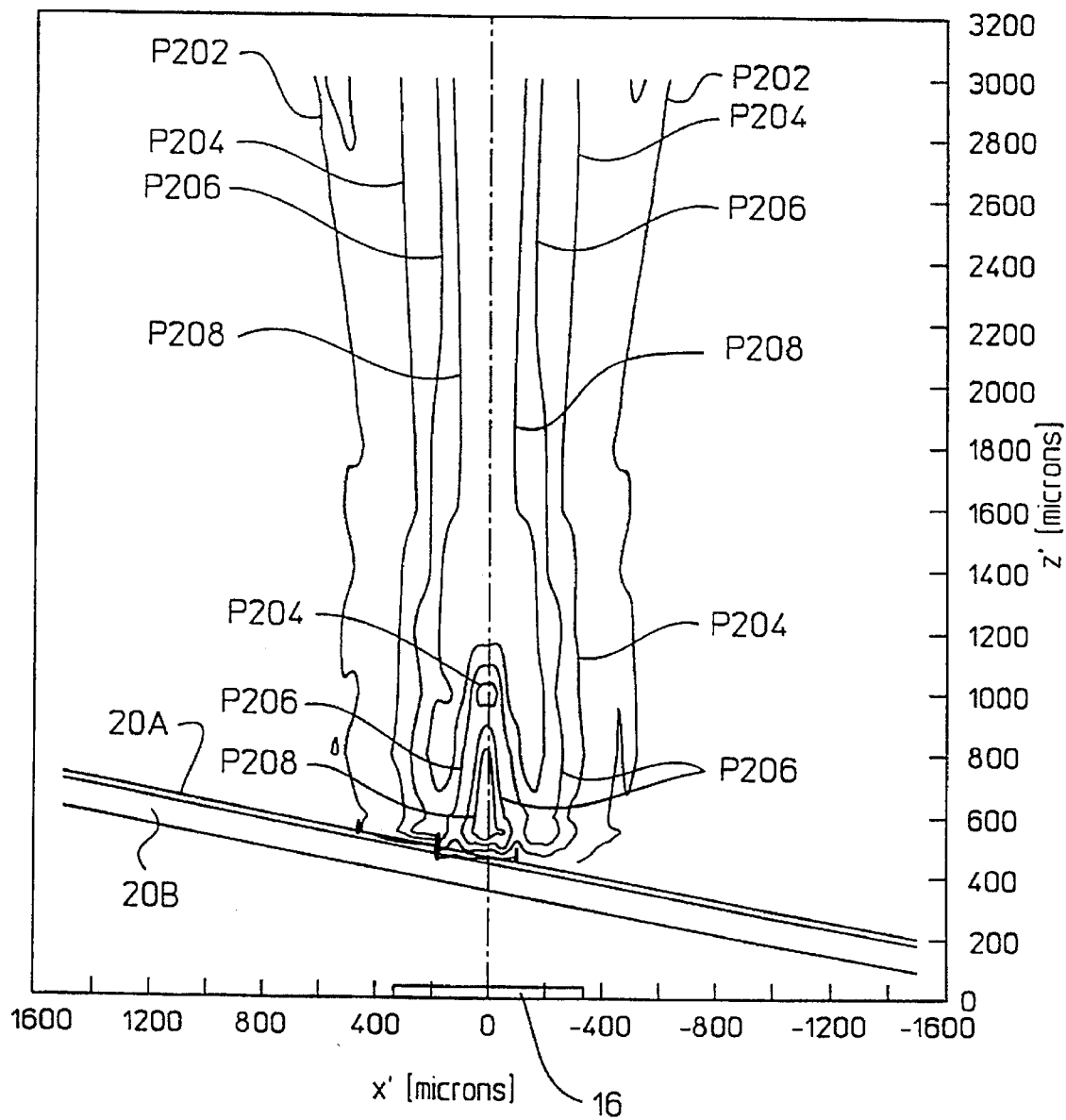
FIG. 5B shows a graphical representation of the calculated elevational pressure contours of a 3.5 French, 30 MHz intravascular catheter having a sheath and no means for compensating for the distorting effect of a sheath.
Figure 5C:
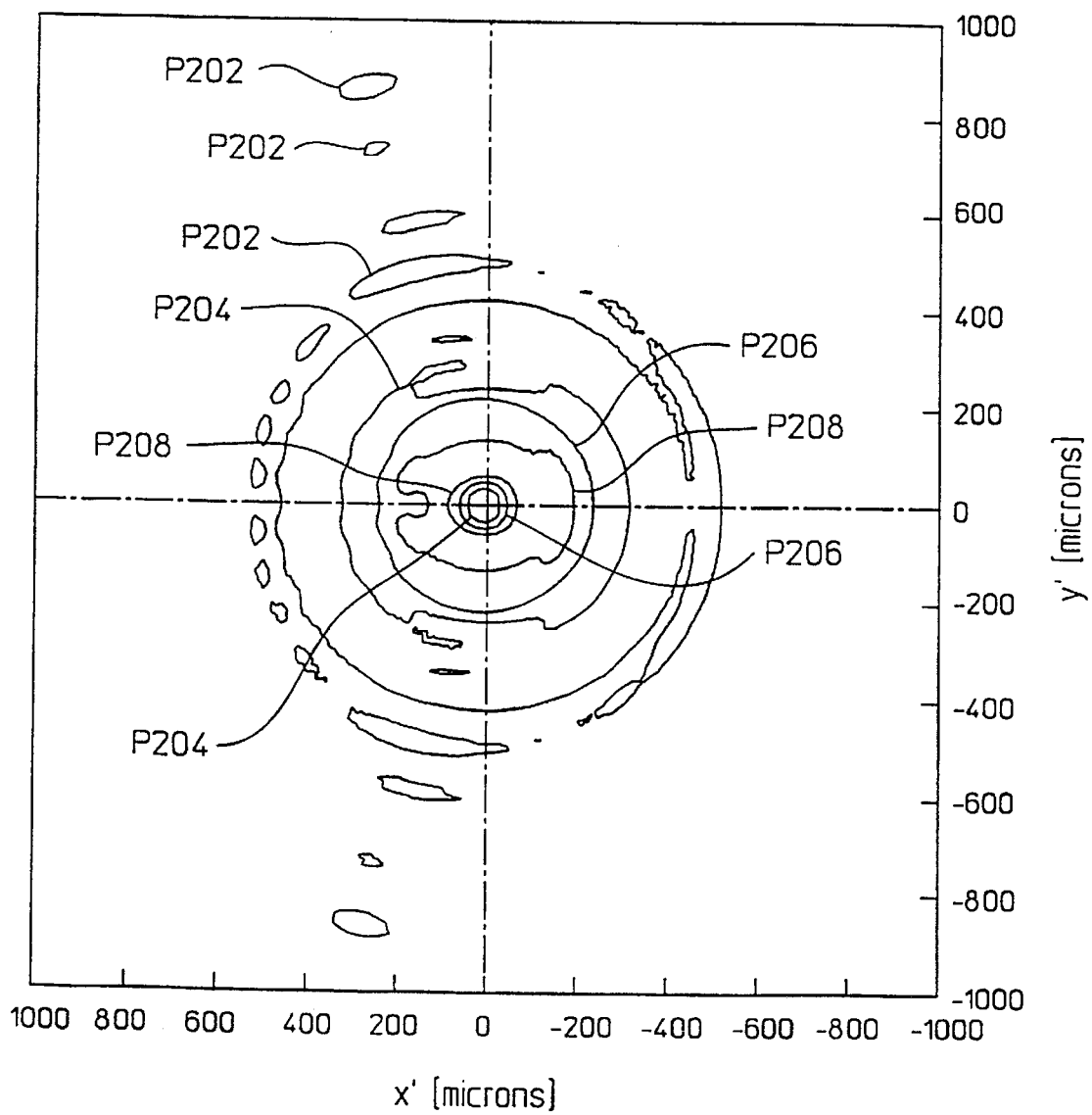
FIG. 5C shows a graphical representation of the calculated pressure contours at a plane at z'=1000 μm of a 3.5 French, 30 MHz intravascular catheter having a sheath and no means for compensating for the distorting effect of a sheath.

FIG. 5 shows calculated pressure contours for a 3.5 French, 30 MHz catheter. The catheter sheath 20 is 1160 μm in diameter and has a 110 μm thick wall. There are two layers (20A, 20B) to the wall: 88 μm thick polyethylene film covered by a 22 μm thick polyurethane. The transducer is tilted to have a 10° (i.e., β=10°) forward look angle. It is also offset by 120 μm from the centerline (or axis) of the catheter. Because of the focusing provided by the sheath, the axial focal point is now located at z'=1910 μm. FIGS. 5A and 5B show pressure contours in the azimuthal and elevational directions, respectively. Unlike the pressure fields shown in FIG. 4, there is now an asymmetry to the beam. This is seen more clearly in FIG. 5C where the pressure contours are shown in a plane lying parallel to the transducer and 1000 μm away. At this distance, one is still in the near-field of the transducer and suffers the deleterious effect of imaging there. For example, the maximum pressure values in FIG. 5C are located off-axis (i.e. not at the center i.e., x'=0, y'=0) of the ultrasonic beam.

Figure 6A:
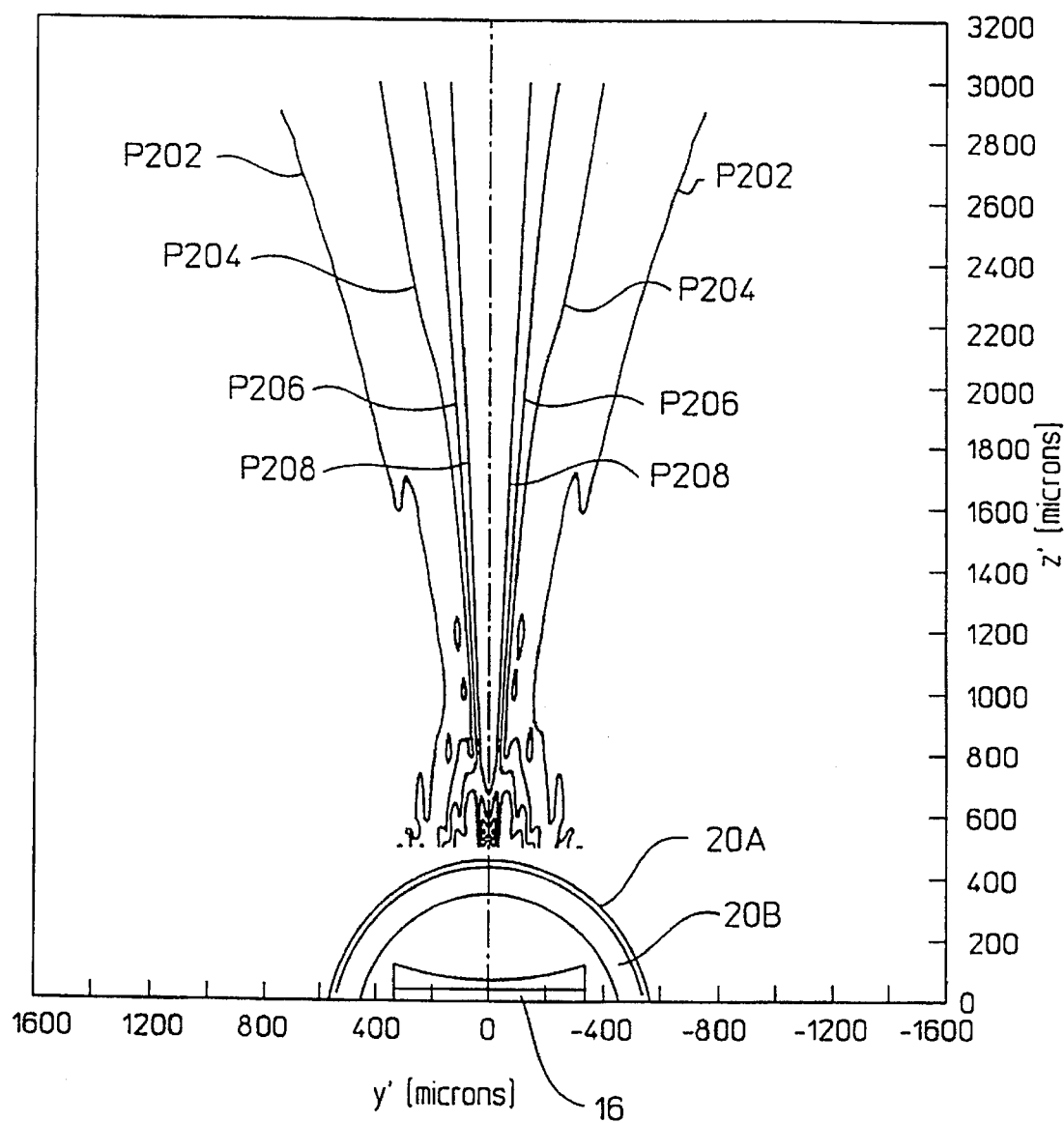
FIG. 6A shows a graphical representation of the calculated azimuthal pressure contours of a 3.5 French, 30 MHz intravascular catheter having a sheath and a plano-concave, spherical lens with 794 μm radius of curvature.
Figure 6B:
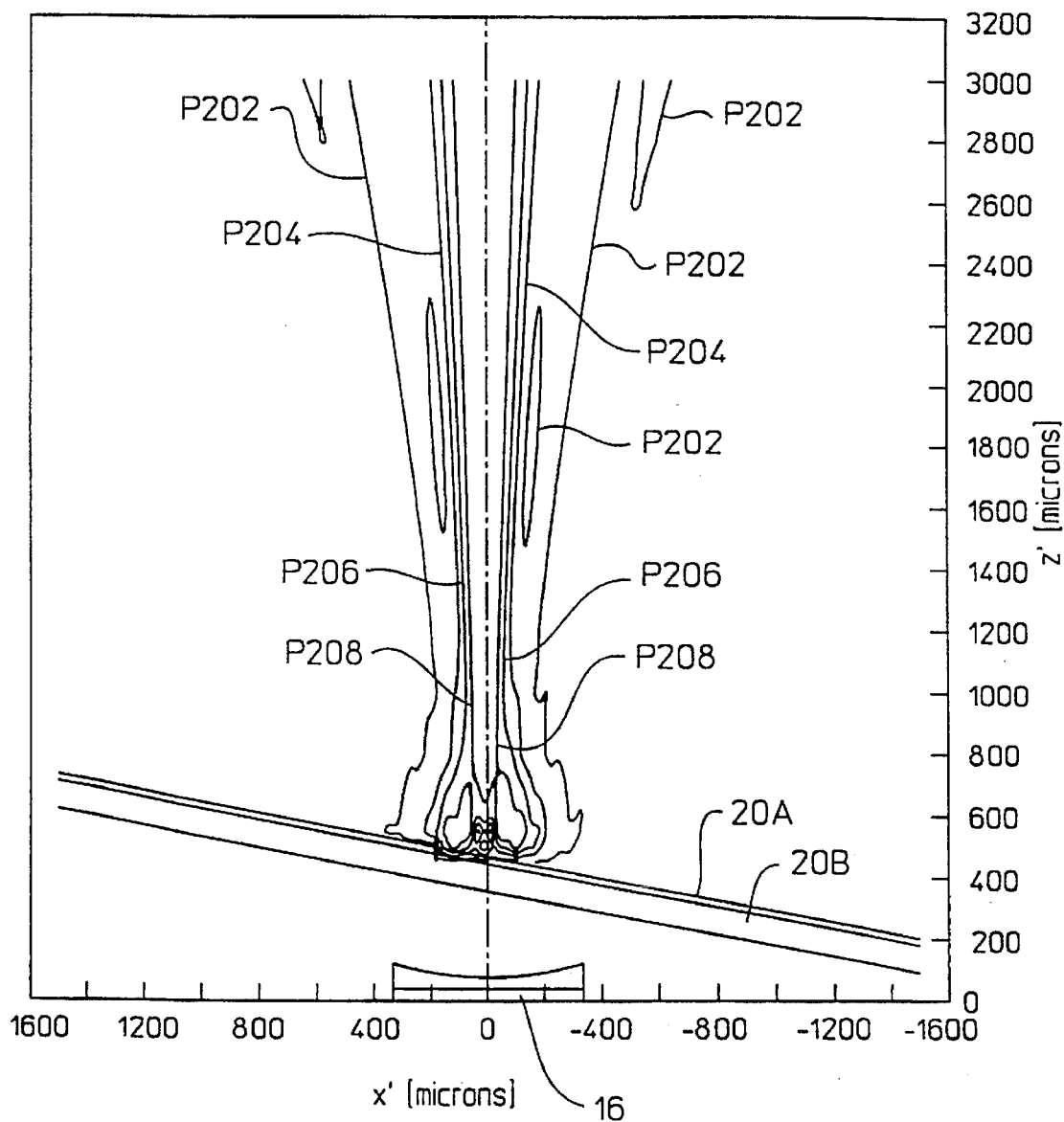
FIG. 6B shows a graphical representation of the calculated elevational pressure contours of a 3.5 French, 30 MHz intravascular catheter having a sheath and a plano-concave, spherical lens with 794 μm radius of curvature.
Figure 6C:
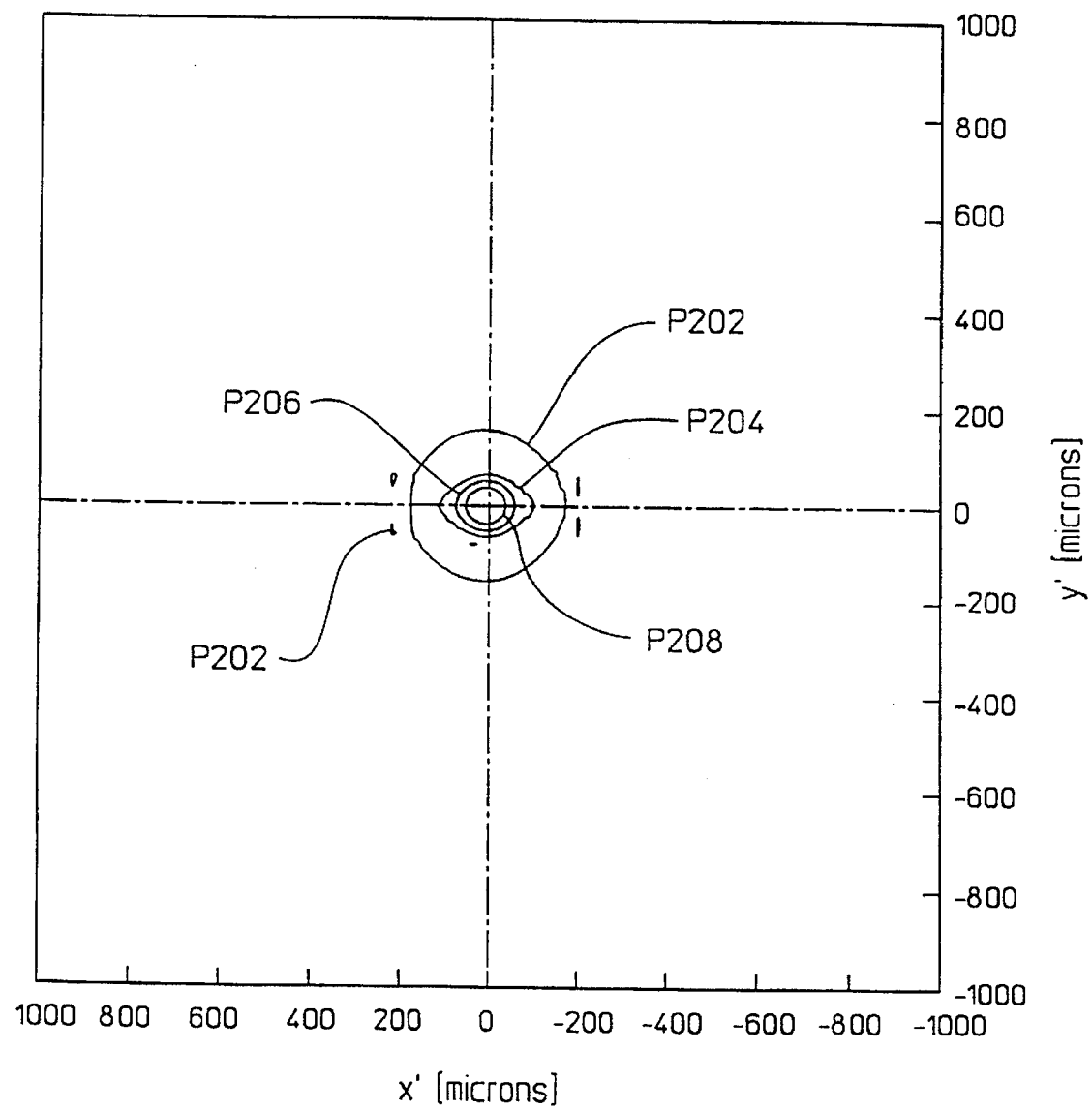
FIG. 6C shows a graphical representation of the calculated pressure contours at a plane at z'=1000 μm of a 3.5 French, 30 MHz intravaseular catheter having a sheath and a plano-concave, spherical lens, with 794 μm radius of curvature.
Figure 7A:
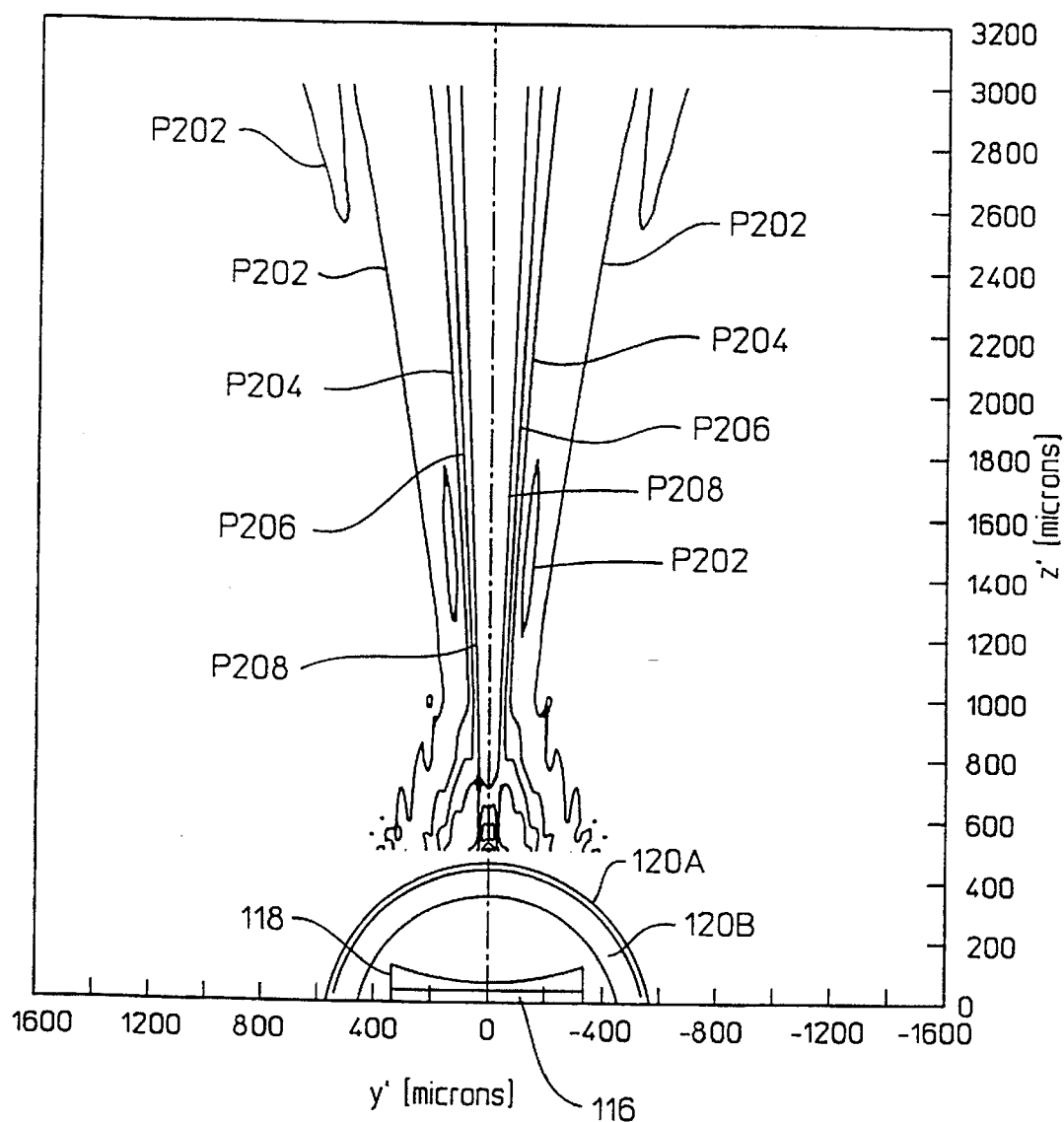
FIG. 7A shows a graphical representation of the calculated azimuthal pressure contours of a 3.5 French, 30 MHz intravascular catheter having a sheath and a plano-concave, aspherical lens.
Figure 7B:
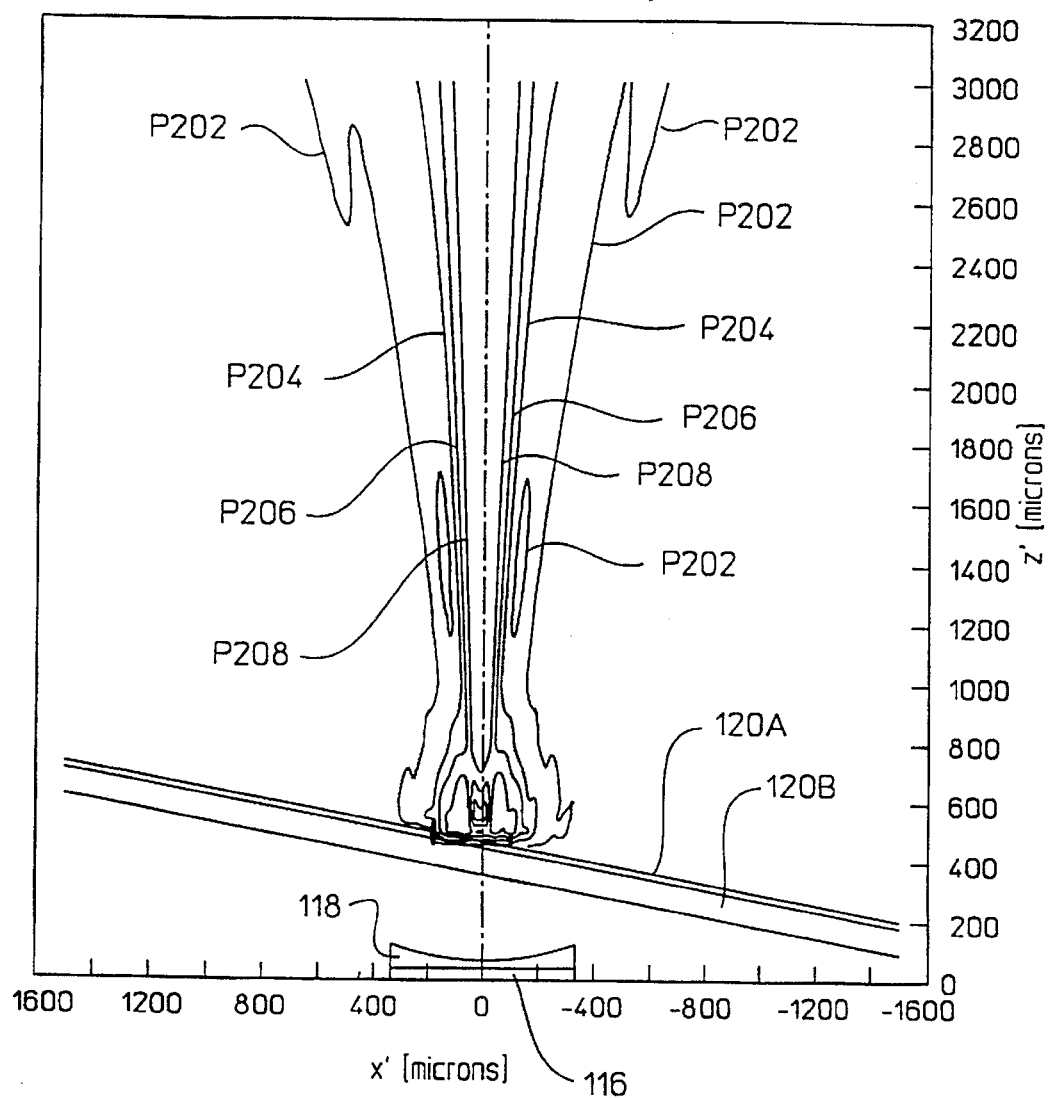
FIG. 7B shows a graphical representation of the calculated elevational pressure contours of a 3.5 French, 30 MHz intravascular catheter having a sheath and a plano-concave, aspherical lens.
Figure 7C:
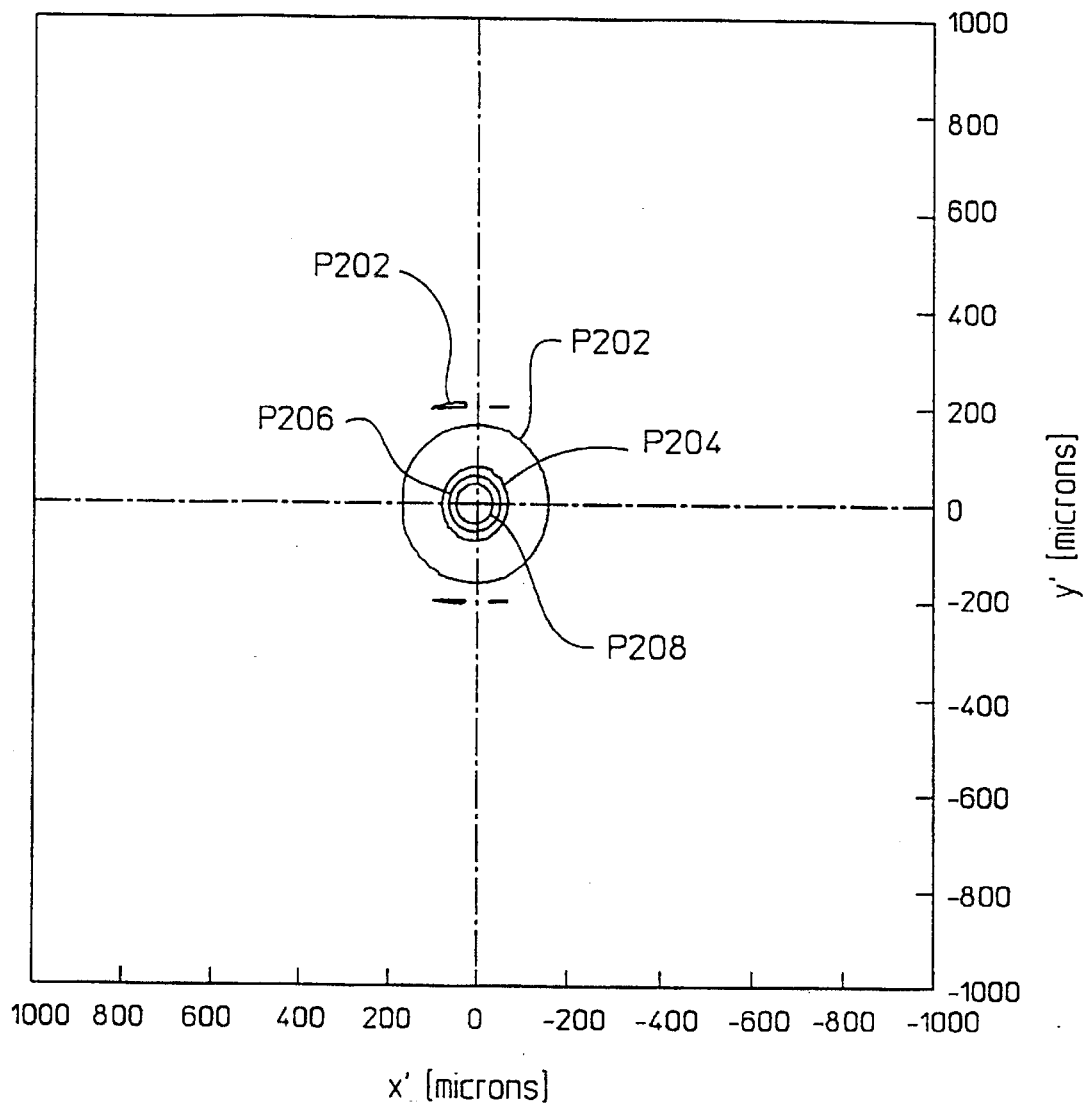
FIG. 7C shows a graphical representation of the calculated pressure contours at a plane at z'=1000 μm of a 3.5 French, 30 MHz intravascular catheter having a sheath and a plano-concave, aspherical lens.
Figure 7D:
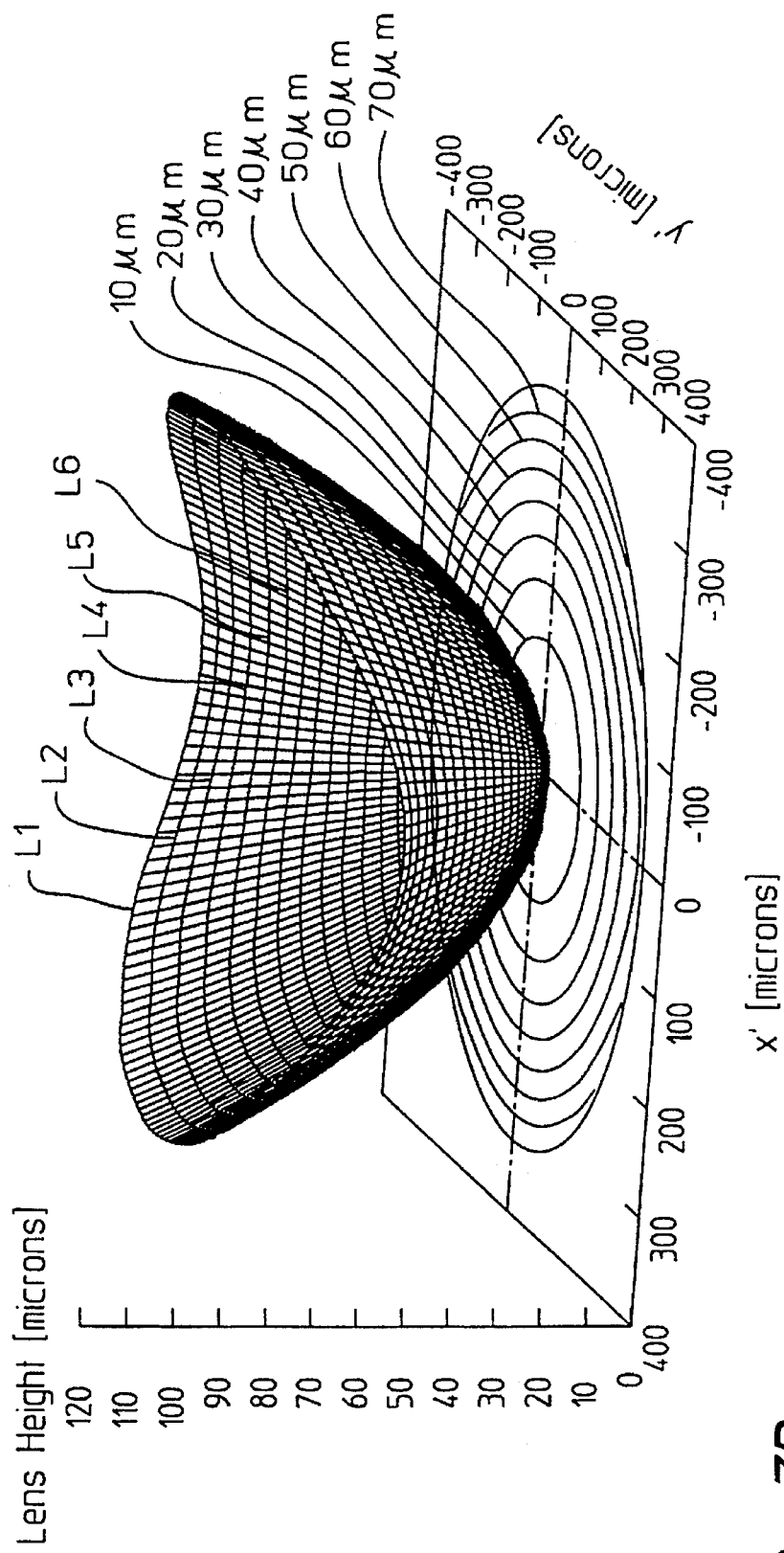
FIG. 7D shows a graphical representation of the calculated shape of an aspherical lens assumed to be made of epoxy, which is used to produce the pressure contours of FIGS. 7A–7C.

For comparison, FIG. 6 shows calculated pressure contours for the same catheter as FIG. 5 except for the addition of a plano-concave focusing lens (diameter of lens=diameter of transducer=0.67 mm, spherically-shaped concave surface whose radius of curvature=794 μm). As expected, the addition of the focusing lens has drawn the focal zone closer to the transducer and narrowed its lateral dimensions. Nevertheless, there remains the problem of an asymmetry to the field as evidenced in FIG. 6C.

FIG. 7 summarizes the application of the technique the present invention to the catheter of FIG. 6. The target focal zone was set to locate the focal zone on-axis and at the axial distance z'=1000 μm. To achieve this focus required a lens whose height is depicted in FIG. 7D for a lens made of a material with a longitudinal wave velocity of 2.82 (i.e., $V_{lens}$=2.82) mm/μsec. A suitable material is epoxy. Thus, an aspherical lens (with greater curvature in the elevational direction than in the azimuthal direction, thereby compensating for the distortion effect of the sheath by augmenting the focusing effect in the elevational direction) provides the symmetric pressure fields shown in FIGS. 7A, 7B, and 7C. For example, the pressure contours (lines p202, p204, p206, p208) shown in FIG. 7C are essentially circles, which correspond to the general shape of the disk-shaped transducer. In FIG. 7D, the lens height axis shows the heights (represented by lines L1 to L6, etc.) above the x'y' plane (the planar side of the lens) for locations on the concave surface of the lens. The contour lines in the x'y' plane show isoheight contours in 10 μm increments.

Shaping the Aspherical Means

Using an ultrasound probe such as that of FIG. 3, ultrasound can be focused through a catheter sheath by compensating for the distorting effect of the sheath. Lalonde et al. (*IEEE UFFC*, 1993, 40(5), pp 592–602) use a similar technique in the design of lenses for hyperthermia applications by assuming a homogenous medium (i.e., no intervening sheath). The calculation of lens dimension reported by Lalonde et al. is incorporated by reference herein. Adapting this method in the present invention, one begins by choosing a target focal point (or a group of closely located points) which lies somewhere outside of the catheter sheath. A pseudo source is placed at this target focal point and the pressure fields are propagated backward towards the transducer using the Rayleigh-Sommerfeld diffraction integral (Acoustic Waves, G. S. Kino, Prentice-Hall, 1987, pp 154–163):

$$\phi(x,y,z) = \frac{1}{2\pi} \iint_S u_z(x',y',z') \frac{e^{-jkR}}{R} dS' \quad (2a)$$

in the case of a rigid baffle and $$\phi(x,y,z) = \frac{jk}{2\pi} \iint_S \phi(x',y',z') \frac{e^{-jkR}}{R} \cos\theta \, dS' \quad (2b)$$

in the case of a compliant baffle. In Equations (2a) and (2b), x', y', and z' refer to the Cartesian location of a source point coordinate, x, y, and z refer to the location of a field point different from point (x', y', z'), $\phi(x, y, z)$ is the velocity potential at the field point (x, y, z), $U_z(x', y', z')$ is the particle displacement of the incremental source element, k is the wave number, R is the distance between the incremental source element at point (x', y', z') and the field point (x, y, z), θ is the angle between the outward normal to dS' and the vector R, and dS' is the area of the incremental source element. In the present invention, for example, where the transducer aperture is approximately 13 wavelengths wide, the results obtainable with either Equation (2a) or Equation (2b) do not differ significantly from the other. Thus Equation (2a) is used for calculations related to the FIGS. 4–7. A person skilled in the art, based on this disclosure, will know how the above equations can be applied.

The velocity potential $\phi(x, y, z)$ determines the particle displacement and consequently the particle velocity. Pressure is related to the particle velocity through the acoustic impedance. A person skilled in the art would be able to relate $\phi$ to particle displacement and pressure. By repeatedly applying the Rayleigh-Sommerfeld diffraction integral, sound may be propagated through a catheter sheath. The values of velocity potential at selected field points are used as sources for subsequent applications of the Rayleigh-Sommerfeld diffraction integral to calculate the velocity potential at another set of points. Backward propagation of the pressure fields to the transducer is a multistep process where the field values output for one step become the input source values in the subsequent step. Propagation of sound from the transducer outward is arbitrarily considered as the forward direction. The steps taken in the backward propagation of acoustical fields (pressure fields) are (assuming a sheath of a single layer):

(a) target focal point→outer surface of the sheath;
(b) outer surface of the sheath→inner surface of the sheath;
(c) inner surface of sheath→plane at the face of the planar transducer.

If the sheath has multiple layers, the back propagation is followed from one layer to the next in a likewise manner until the sheath has been traversed. Continuity of the particle displacement normal to the boundary is applied at each interface encountered.

Upon reaching the transducer, the dimensions, i.e., the shape of the aspherical lens can be determined to test the effect of the aspherical lens. The pressure fields on the face of the transducer are complex conjugated and forward propagated in an analogous fashion to the backward propagation. The resulting pressure field outside of the sheath is compared to that on the target focal point(s) that were initially supplied. If necessary, the pseudo source is modified and the procedure iterated.

How the excitation at the transducer required to achieve the desired focus is approximated depends on the type of IVUS catheter in use. For a multielement synthetic aperture catheter the relative phase of each element is adjusted as indicated by the results of the backward propagation. For a single element transducer, the transducer itself can be made concave, or a planar transducer can be cut with different dimensions in the azimuthal and elevational directions (i.e., an elliptically shaped transducer).

Preferably, a lens is used in combination with a planar transducer driven in a piston mode. In the last case, the required height of a plano-concave lens (assuming the speed of sound in the lens is greater than that in the coupling medium, say water) is given by:

$$\text{height}(x',y') = \text{required phase shift}(x',y') \times \frac{V_{lens} V_{water}}{(V_{lens} - V_{water}) 2\pi f} \quad (3)$$

where the required phase shifts are obtained from the fields at the transducer face (or surface) after back propagation, $V_{lens}$ and $V_{water}$ are the speed of sound in the lens material and water respectively, and f is the operating frequency of the transducer.

Figure 8A:
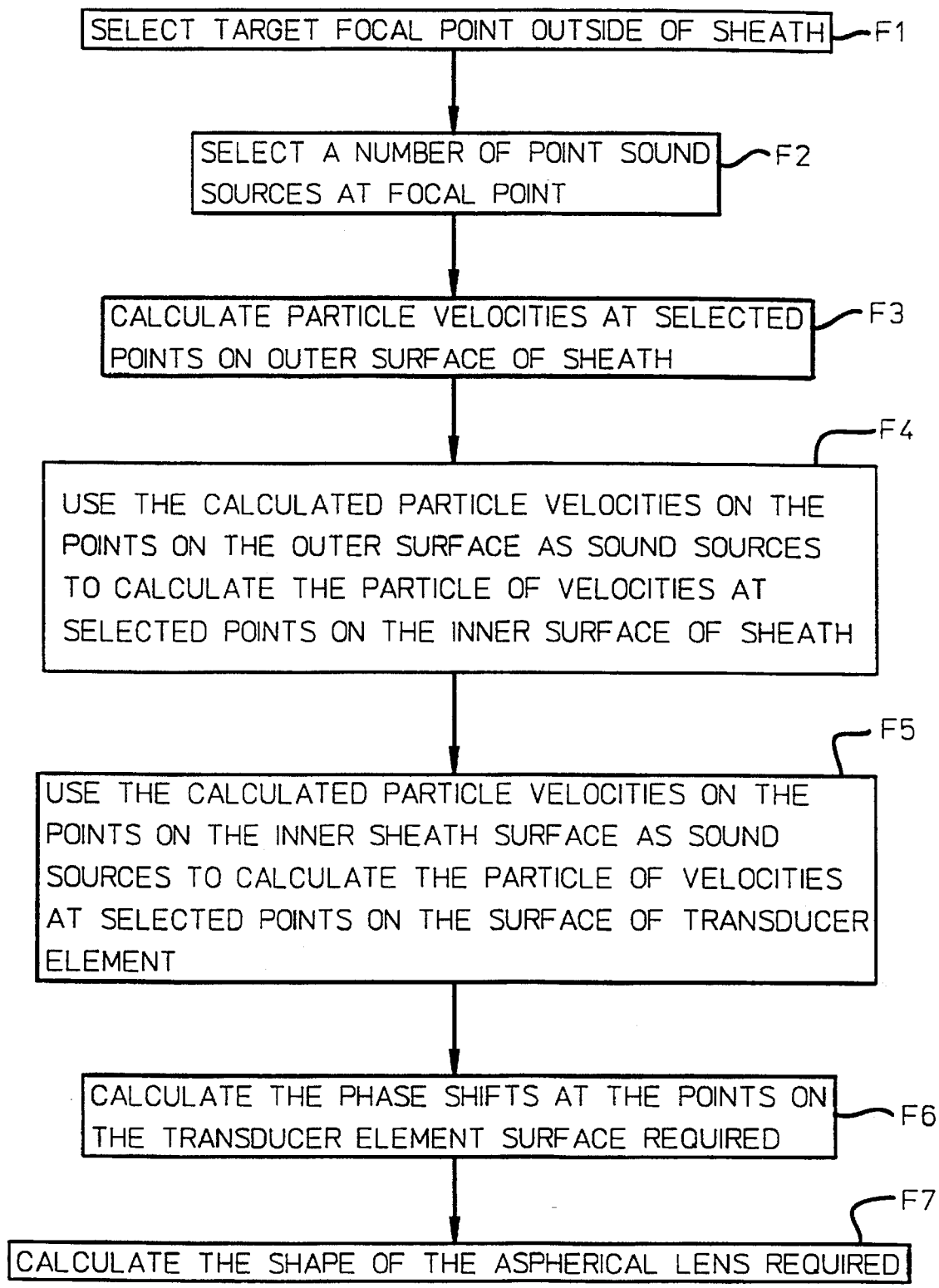
FIG. 8A shows a flow chart for the process of calculating the shape of the aspherical lens.
Figure 8B:
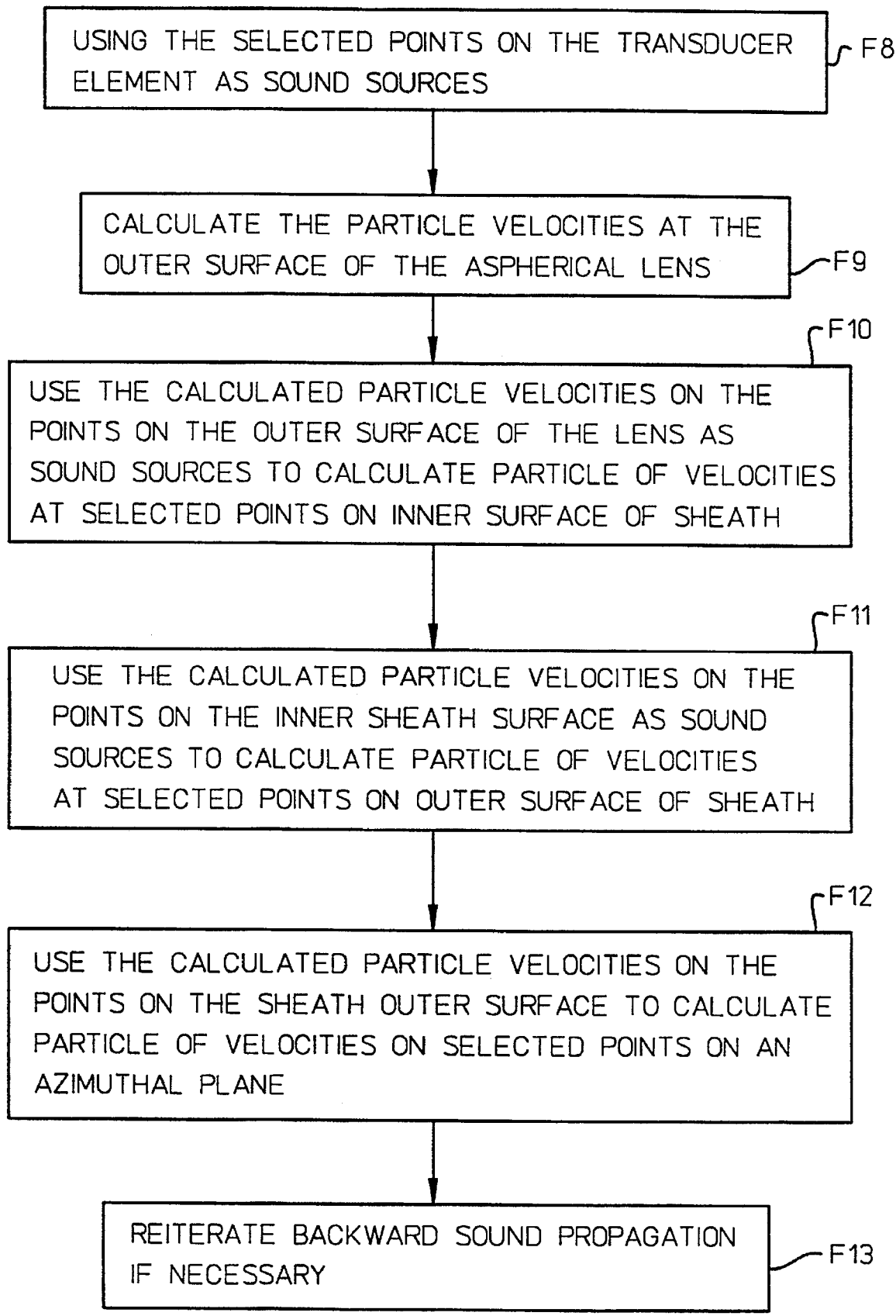
FIG. 8B shows a flow chart for the process of confirming the calculated shape of the aspherical lens.

The steps of determining the curvature of the aspherical lens are shown in the flow diagrams of FIG. 8A and FIG. 8B. In detail, as shown in FIGS. 9A to 9C and FIGS. 10A to 10C, the technique is as follows.

Figure 9A:
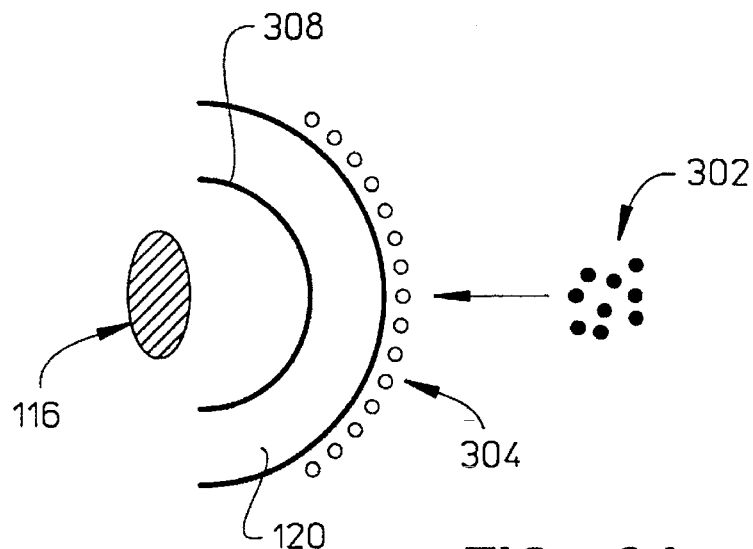
FIGS. 9A, 9B, and 9C show, respectively, the propagation of sound from a selected focal point to the outer surface of the sheath, from the outer surface of the sheath to the inner surface of the sheath, and from the inner surface of the sheath to the transducer.

1. In FIG. 9A, a target focal point lying somewhere outside of the catheter sheath is selected (block F1 shown in FIG. 8A). A hypothetical point source (or small number of hypothetical point sources) 302 are placed at the target focal point (Block F2). These sources 302 are used as inputs to the Rayleigh-Sommerfeld diffraction integral and are used to determine the pressure and particle velocity at a set of points 304 on the outer surface of the catheter sheath 120 (block F3). The arrow in FIG. 9A shows the hypothetical propagation of sound. Likewise, the arrows in FIG. 9B to FIG. 10C show the hypothetical propagation of sound.

Figure 9B:
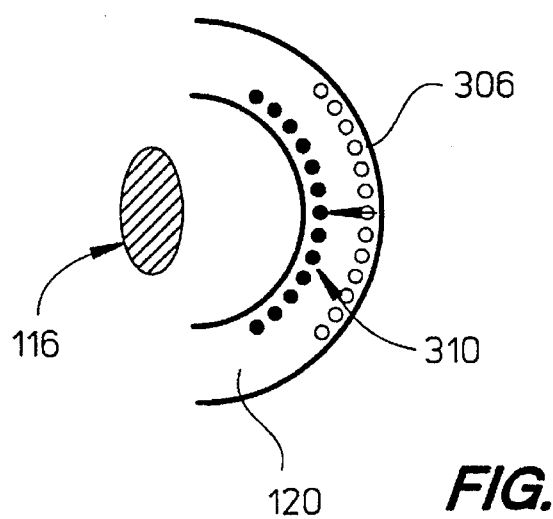

2. In FIG. 9B, the pressures or particle velocities thus calculated at discrete points 304 on the outer surface of the sheath 120 are then used as sources 306 in the Rayleigh-Sommerfeld diffraction integral by invoking the continuity of particle displacement at that interface (i.e., substituting in the boundary condition) and propagating sound to the next layer of the sheath has more than one layer, not shown in the figures) of the sheath (block F4).

3. Step 2 is repeated, once for each layer for a multilayer sheath, until the inner surface 308 of the sheath is reached (at a set of points 310).

Figure 9C:
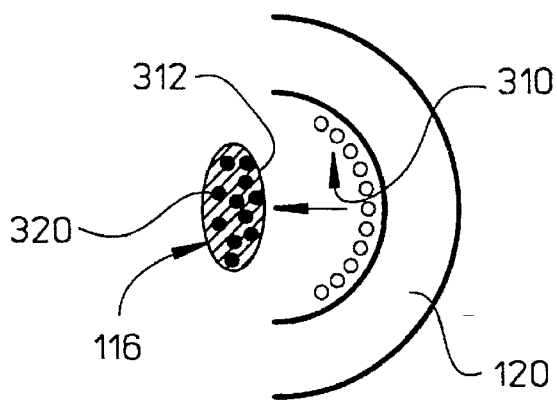

4. In FIG. 9C, sound is then propagated from the inner surface of the sheath (from points 310) to the face 312

(having points 320) of the transducer hypothetically using the velocity potential calculation by applying the Rayleigh-Sommerfeld diffraction integral (block F6). The phase shifts at the points on the transducer surface is calculated (block F6).

5. The shape of an aspherical lens is calculated (block F7). The complex conjugate of the calculated particle velocity determined in Step 4 is the excitation required for a wave propagating forward from the face of the transducer to focus at the axial location selected in Step 1. How realistically this excitation function can be generated depends on the type of transducer being used. If the synthetic aperture approach is desired, the amplitude and phase of each of a plurality of elements can be adjusted to achieve the desired focal characteristics. Intravascular imagers commonly employ a flat, single element transducer operating in "piston mode" where all points on the face of the transducer move in phase and with equal amplitude. The necessary spatial variation in the amplitude and phase of the particle velocity across the aperture must therefore be achieved physically rather than electronically. One might, for example, apodize the transducer to approximate the required spatial amplitude variation. Furthermore, the required spatial variation in the phase of the particle velocity may be achieved by placing a lens with one planar face against the face of the transducer. The height variation (i.e., the thickness) of the lens is determined by Equation (3) described above.

As previously stated, alternative methods of achieving the necessary phase variation include shaping (curving) the transducer to obtain the aspherical shape for transmission or reception of ultrasound and shaping a portion of the sheath to have a portion with an arcuate surface and nonuniform thickness.

Figure 10A:
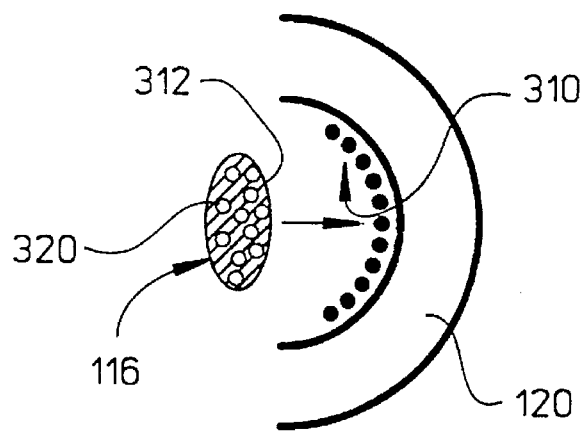
FIGS. 10A, 10B, and 10C show, respectively, the propagation of sound from the transducer to the inner surface of the sheath, from the inner surface of the sheath to the outer surface of the sheath, and from the outer surface of the sheath to the targeted area.
Figure 10B:
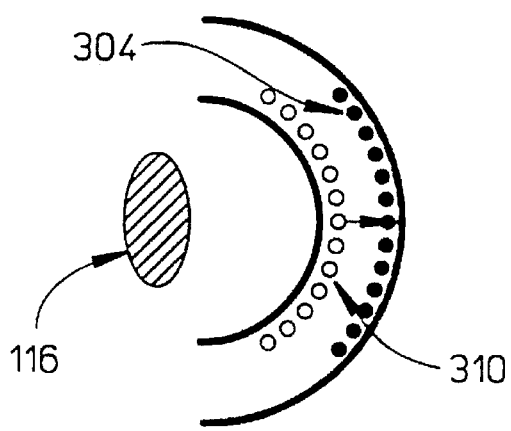
Figure 10C:
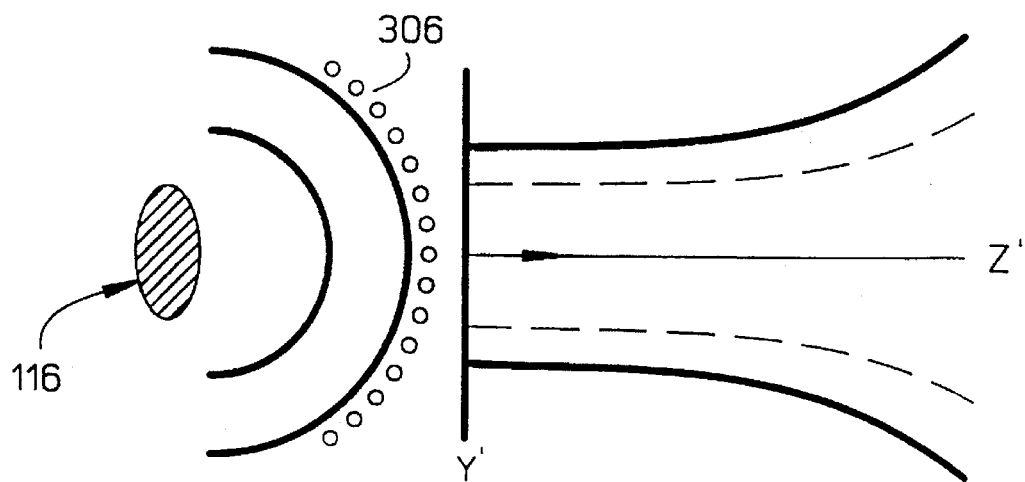

6. As shown in FIGS. 10A–10C, to (optionally) evaluate the effectiveness of the aspherical means to compensate for acoustic distortion by the sheath, a realizable approximation to the required particle velocity across the face of the transducer as was calculated in Step 4 is applied to the transducer. Sound is propagated hypothetically in the forward direction from the face 312 from selected points 320 of the transducer (block F8 of FIG. 8B) to the inner surface 308 of the sheath 120 as if through an aspherical lens by calculating the particle velocities in a manner analogous to the backward propagation of sound. This is done by maintaining the pressure field obtained in Step 4 (with phase shifts) on points 320 on the transducer to propagate sound to the sheath (combining blocks F9, F10 of FIG. 8B). Alternatively, calculation can be done based on hypothetical propagation of sound to the outer surface of the aspherical lens (block F9) and then propagating to the inner surface of the sheath (block F10). In this case, the points 320 of the transducer preferably vibrate without phase shifts.

7. The pressure or particle velocity just calculated at discrete points 310 on the inner surface of the sheath are then used as sources in the Rayleigh-Sommerfeld diffraction integral, invoking the continuity of particle displacement at that interface, and propagating sound to the next layer of the sheath.

8. Step 7 is repeated until the outer surface of the sheath (at a set of points 304) is reached.

9. Sound is propagated hypothetically from the outer surface of the sheath 120 to points exterior to the sheath. Pressure field calculations in an azimuthal plane, an elevational plane, and axial planes at varying ranges are particularly useful to visualize the three dimensional extent of the beam. Pressure contour lines of the calculated fields will estimate the ability to resolve structures in the tissue being imaged.

10. The focal zone parameters (i.e. velocity potential, and therefore the pressure field) determined in Step 9 are compared to the target focus specified in Step 1.

11. The procedure is iterated by slightly moving the target focal zone or the height of the aspherical lens until satisfied with the beam profile.

By the above method, the curvature of the aspherical lens (preferably with a planar surface for coupling with a planar transducer) can be calculated. Because of the simplicity of construction, the preferred ultrasonic probe has such a plano-concave aspherical lens with a flat, single element transducer. The size of the aspherical lens depends on the size of the transducer. Such an aspherical lens can then be made from an appropriate material such as glass, polymeric materials, metal, and the like. Catheters with focal zone distances within the range of, for example, about 500 µm to 3000 µm can be made for 3.5 French catheters operated at equal to or greater than 20 MHz. Conventional processes for making aspherical acoustic lenses, such as molding, or grinding can be used. The application of the present invention is not limited by the materials or processes of making the aspherical lens from such materials.

Figure 11:
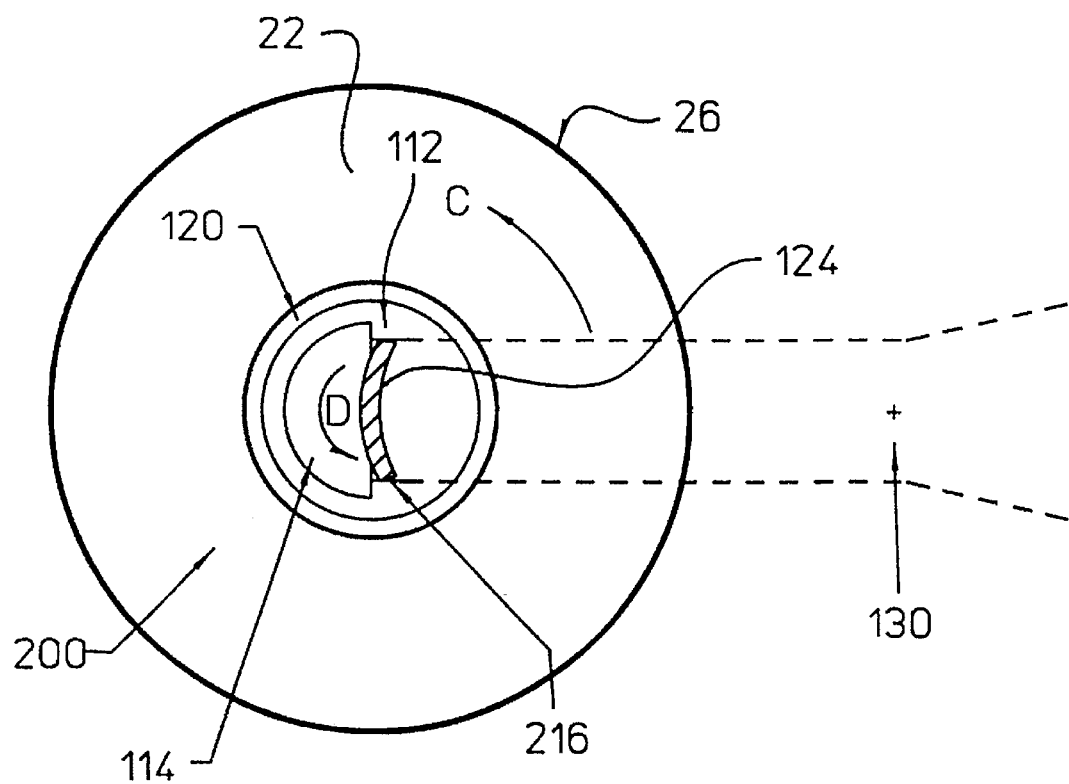
FIG. 11 shows a lateral cross-sectional view of another embodiment of the ultrasound probe of the present invention positioned inside a blood vessel.

As previously described, aspherical means other than a lens can be used to reduce the distorting effect of the sheath. For example, a probe 200 having a transducer 216 with an arcuate, concave, and aspherical radiating surface 124 is shown in FIG. 11. In this case, no lens will be required. Although multielement transducers can be used, in this embodiment, the transducer 216 has a single transducer element. Based on the calculated particle displacements on the transducer, the shape of the transducer that is needed to compensate for the distorting effect of the sheath on ultrasound can be calculated in a manner analogous to that used for the aspherical lens.

Figure 12:
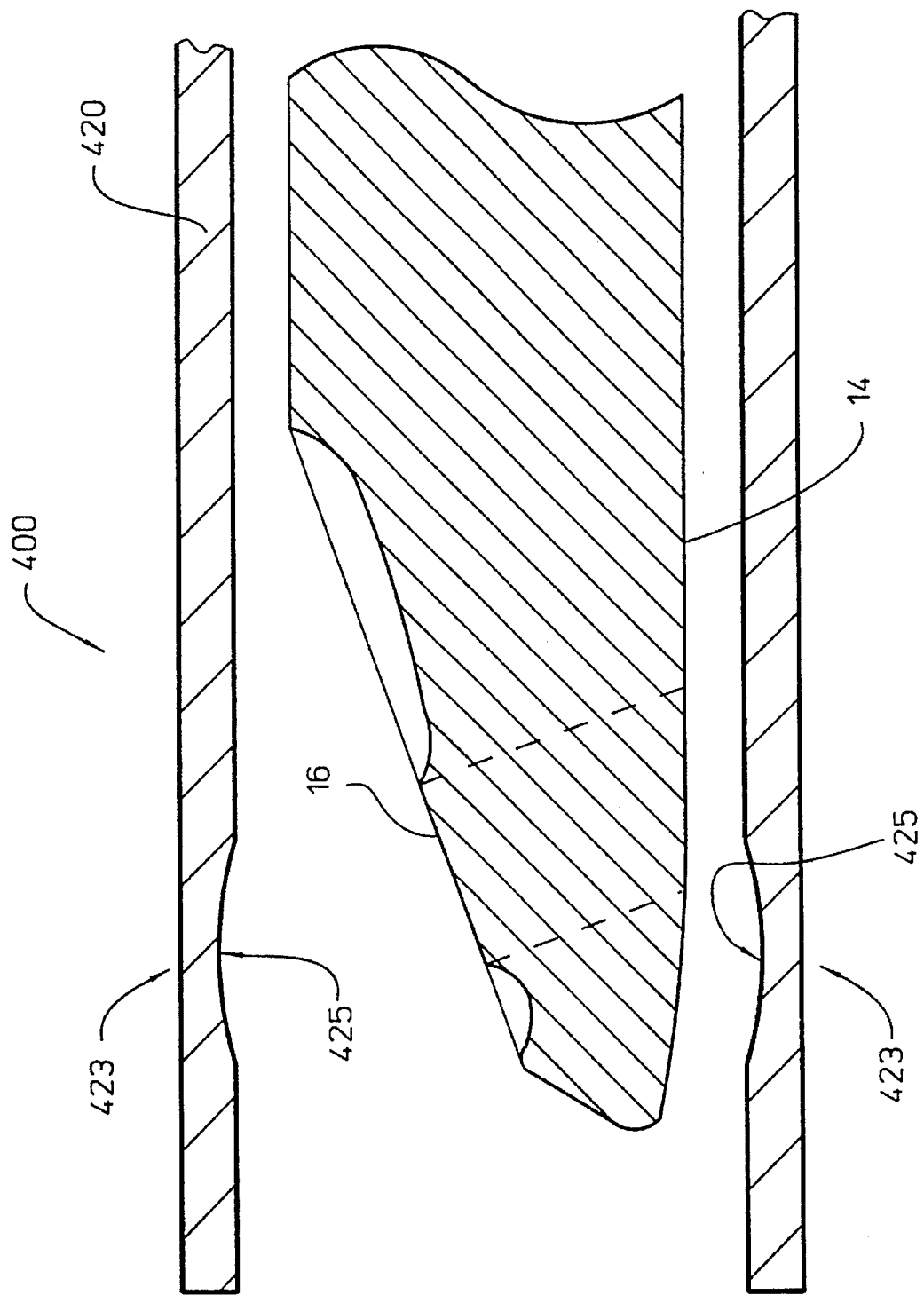
FIG. 12 shows a longitudinal cross-sectional view in portion of yet another embodiment of the ultrasound probe of the present invention.

Further, as shown in FIG. 12, instead of using a lens or curving the transducer radiating surface, the dimensions of the sheath can be modified to reduce the distorting effect on ultrasound. In this case, the probe 400 includes a sheath 420 having a portion 423 that has a nonuniform thickness. This portion 423 has a groove 425 positioned at where an ultrasonic beam emitted from the transducer 16 would be directed (as the shaft is rotated). The groove 425 surrounds the axis of the sheath 420 and has a surface which is not spherical (i.e., aspherical). The portion 423 of the sheath 420 shown in FIG. 12 is a preferred embodiment having a straight external boundary and an inner surface with an arcuate boundary on a cross section along the axis of the sheath. Based on the particle displacements on the transducer, the shape of the portion 423 needed so as not to produce (in other words, to compensate for) the distorting effect of a sheath of uniform thickness on ultrasound can be calculated in a manner analogous to the above method for the aspherical lens.

Although the illustrative embodiments of the present invention have been described in detail, it is to be understood that the above-described embodiments can be modified by one skilled in the art, especially in sizes and shapes and combination of various described features without departing from the spirit and scope of the invention. For example, the aspherical lens can be positioned so it does not contact the transducer directly. Also, transducers of nondiskshaped dimensions (e.g., square, ellipsoidal, etc.) can also be used. Probes applicable for a variety of frequencies are contemplated.

What is claimed is:

1. A method for focusing a beam of ultrasound at a target area of an object using an intraluminal ultrasonic probe with a substantially cylindrical case around a transducer of the probe, wherein the substantially cylindrical case has a central axis and the transducer is rotatable about the central axis of the case, said method comprising:

(a) emitting the beam of ultrasound from the transducer; and (b) focusing the beam of ultrasound with an aspherical means having an spherical surface and transmitting the beam of ultrasound through the substantially cylindrical case to reduce the distorting effect by the case on the beam of ultrasound.

2. The method according to claim 1 wherein the aspherical means is an aspherical lens disposed between the transducer and the substantially cylindrical case.

3. The method according to claim 1 wherein the aspherical shape of the aspherical means is determined by a method including: selecting a focal point at the target area as a hypothetical source of a beam of ultrasound, calculating the velocity potential on the transducer based on said beam of ultrasound, and calculating the aspherical shape of the aspherical means based on said velocity potential.

4. The method according to claim 3 wherein the substantially cylindrical case has substantially cylindrical surfaces and the aspherical shape of the aspherical means is determined by a method including: selecting the focal point at the target area, calculating the velocity potentials on the substantially cylindrical surfaces of the case, and then calculating the velocity potential on the transducer.

5. The method according to claim 4 wherein the velocity potential on the substantially cylindrical surface of the substantially cylindrical case more proximal to the axis of the case is calculated based on the velocity potential on the substantially cylindrical surface of said case more distal to said axis.

6. The method according to claim 3 wherein the substantially cylindrical case has at least two layers each having substantially cylindrical surfaces and the aspherical shape of the aspherical means is determined by a method including: selecting the focal point at the target area and calculating the velocity potentials on the substantially cylindrical surfaces of each layer of the substantially cylindrical case and then calculating the velocity potential on the transducer.

7. The method according to claim 6 wherein the velocity potentials on the substantially cylindrical surfaces of the layers more proximal to the axis of the substantially cylindrical case is calculated based on the velocity potentials on the surfaces of the layers more distal to said axis.

8. The method according to claim 3 wherein the velocity potential on a surface on the substantially cylindrical case is calculated by applying the Rayleigh-Sommerfeld diffraction integral.

9. The method according to claim 3 wherein the shape of the aspherical means is calculated to compensate for phase shifts due to the substantially cylindrical case, the aspherical shape of the aspherical means being calculated by determining the phase shifts at a plurality of locations on the transducer from a hypothetical source at the selected focal point at the target area transmitting an ultrasonic beam through the case to the plurality of locations on the transducer.

10. The method according to claim 3 wherein the shape of the aspherical means is calculated by a method including: confirming the shape of the aspherical means by further calculating the velocity potentials on the surfaces of the substantially cylindrical case from a plurality of hypothetical ultrasound sources on the transducer and then calculating the velocity potentials at a plurality of locations on a surface at the selected focal point at the target area at which the original hypothetical ultrasound source is located.

11. The method according to claim 1 wherein the transducer is positioned to direct the ultrasound in a direction about 0° to 30° from the normal to the shaft axis.

12. The method according to claim 1 wherein the aspherical means is a transducer having an arcuate aspherical radiating surface which emits said beam of ultrasound.

13. The method according to claim 1 wherein the aspherical means is a portion of the substantially cylindrical case having a groove around the central axis of said case with an arcuate aspherical surface on the groove to result in non-uniform thickness in said case for focusing said beam of ultrasound.

14. A method of determining the shape of an aspherical means to compensate for a distorting effect of a substantially cylindrical case encircling a transducer in an ultrasound probe for intraluminal application in an object, comprising:

(a) selecting a focal point at a target area as a hypothetical source of a beam of ultrasound;

(b) calculating the velocity potential on the transducer based on said beam of ultrasound having traveled through said substantially cylindrical case; and (c) calculating the aspherical shape of the aspherical means based on said velocity potential.

15. The method according to claim 14 wherein the substantially cylindrical case has substantially cylindrical surfaces and the method further comprising calculating the velocity potentials on the substantially cylindrical surfaces of the case and then calculating the velocity potential on the transducer based on the velocity potentials on the substantially cylindrical surfaces of the case.

16. An ultrasound probe for intraluminal application comprising:

(a) a substantially cylindrical acoustic case having a central axis for insertion in a lumen of an object;

(b) an ultrasonic transducer unit positioned in said acoustic case and rotatable about said central axis of said acoustic case to transmit or receive ultrasonic beams in a direction at an angle to said central axis, said transducer unit comprising:

(i) transducer for generating or receiving ultrasound;

(ii) shaft, operatively connected with the transducer and having an axis substantially coincident with said central axis for rotating the transducer around said central axis; and (iii) aspherical means associated with the transducer in said acoustic case, said aspherical means having an aspherical surface to reduce the distortion by the substantially cylindrical acoustic case on ultrasound beams focused at a target area.

17. The ultrasound probe according to claim 16 wherein the aspherical means is an aspherical lens that substantially compensates the distorting effect of the substantially cylindrical case.

18. The ultrasound probe according to claim 16 wherein the aspherical shape of the aspherical means is such that selecting a plurality of hypothetical sources on a circularly shaped transducer and calculating the velocity potential on surfaces of the substantially cylindrical case based on a hypothetical ultrasound beam emitted by the transducer and then calculating the velocity potential on a focal surface normal to the beam at a selected focal point will result in a velocity potential profile of substantially circular shape on the focal surface.

19. The ultrasound probe according to claim 16 wherein the aspherical shape of the aspherical means results in a phase shift in ultrasound transmission substantially equal to the phase shift calculated by a method including: selecting the focal point at the target area as a hypothetical ultrasound source, calculating the velocity potentials on the surfaces of the substantially cylindrical case and then calculating the velocity potential on the transducer.

20. The ultrasound probe according to claim 19 wherein the velocity potential on a surface of the substantially cylindrical case more proximal to the central axis of the case is calculated based on the velocity potential on a surface of said case more distal to said axis.

21. The ultrasound probe according to claim 16 wherein the substantially cylindrical case has at least two layers and the aspherical shape of the aspherical means is determined by a method including: selecting a focal point at the target area as a hypothetical ultrasound source and calculating the velocity potentials on surfaces of each layer of the sheath and then calculating the velocity potential on the transducer.

22. The ultrasound probe according to claim 16 wherein the aspherical means is a transducer having an arcuate aspherical radiating surface which generates or receives said beams of ultrasound and substantially compensates the distorting effect of the substantially cylindrical case.

23. The ultrasound probe according to claim 16 wherein the aspherical means is a portion of the substantially cylindrical case having a groove around the central axis of said case with an arcuate aspherical surface on the groove to remit in nonuniform thickness in said case for focusing said beam of ultrasound such that said case results in substantially reduced distortion compared to a substantially cylindrical case without such a groove.

24. A method of making an ultrasound probe having a substantially cylindrical case for intraluminal application in an object, comprising:
 (a) mounting a transducer on a rotatable shaft having an axis to form a rotatable unit for rotatably transmitting or receiving ultrasound;
 (b) securing an aspherical lens having an aspherical surface to said rotatable unit; and
 (c) positioning said aspherical lens and said rotatable unit inside the substantially cylindrical case having an axis substantially coincidental to the axis of the shaft for rotatable transmission or reception of ultrasound in the case such that the distorting effect on ultrasound beams by the substantially cylindrical case is reduced by the aspherical lens.

* * * * *